(12) United States Patent
Tanaka et al.

(10) Patent No.: US 8,217,192 B2
(45) Date of Patent: Jul. 10, 2012

(54) PRODUCTION METHOD OF (2E,6Z,8E)-N-ISOBUTYL-2,6,8-DECATRIENAMIDE (SPILANTHOL), AND FOOD OR DRINK, FRAGRANCE OR COSMETIC, OR PHARMACEUTICAL COMPRISING THE SAME

(75) Inventors: Shigeru Tanaka, Hiratsuka (JP); Kenji Yagi, Hiratsuka (JP); Hideo Ujihara, Hiratsuka (JP); Kenya Ishida, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 355 days.

(21) Appl. No.: 12/673,633

(22) PCT Filed: Jan. 16, 2009

(86) PCT No.: PCT/JP2009/050566
§ 371 (c)(1),
(2), (4) Date: Feb. 16, 2010

(87) PCT Pub. No.: WO2009/091040
PCT Pub. Date: Jul. 23, 2009

(65) Prior Publication Data
US 2011/0105773 A1    May 5, 2011

(30) Foreign Application Priority Data

Jan. 18, 2008  (JP) ................. 2008-009295
Jan. 18, 2008  (JP) ................. 2008-009821
Jan. 18, 2008  (JP) ................. 2008-009832
Jan. 18, 2008  (JP) ................. 2008-009851

(51) Int. Cl.
*C07C 231/00* (2006.01)

(52) U.S. Cl. ............ 554/45; 554/50; 554/61; 554/68; 554/69; 562/840; 568/596

(58) Field of Classification Search .......... 554/45, 554/50, 61, 68, 69; 562/840; 568/596
See application file for complete search history.

(56) References Cited

U.S. PATENT DOCUMENTS 6,248,498 B1    6/2001  Gybin

OTHER PUBLICATIONS

International Search Report (PCT/ISA/210) dated Mar. 3, 2009 in PCT/JP2009/050566.
International Preliminary Examination Report (PCT/ISA/237) dated Mar. 3, 2009 in PCT/JP2009/050566.
Wu et al, "Preparation of 4,4-Dimethoxybutyl Iodide from 1,4-Butanediol via the Corresponding Tosylate," Journal of Organic Chemistry, vol. 59, No. 17, pp. 5076-5077 (1994).
Hazen, "Methoxonium Ions in Solvolysis. Neighboring Acetal Participation," Journal of Organic Chemistry, vol. 35, No. 4, pp. 973-978 (1970).
Wang et al, "Efficient Preparation of Functionalized (E,Z) Dienes Using Acetylene as the Building Block," Journal of Organic Chemistry, vol. 63, No. 12, pp. 3806-3807 (1998).
Ikeda et al, "Stereoselective Synthesis of 1,4-Disubstituted 1,3-Diene from Aldehyde Using Organotitanium Reagent," Tetrahedron, vol. 43, No. 4, pp. 731-741 (1987).
Ikeda et al, "Facile Routes to Natural Acyclic Polyenes Synthesis of Spilanthol and Trail Peromone for Termite," Tetrahedron Letters, vol. 25, No. 45, pp. 5177-5180 (1984).

*Primary Examiner* — Deborah D Carr
(74) *Attorney, Agent, or Firm* — Sughrue Mion, PLLC

(57) ABSTRACT

A problem as an object of the invention is to provide a production method of spilanthol in a large scale without using expensive reagents. The present invention provides a production method of N-isobutyl-2,6,8-decatrienamide, wherein a column chromatography purification step is not required in all processes.

16 Claims, No Drawings

PRODUCTION METHOD OF (2E,6Z,8E)-N-ISOBUTYL-2,6,8-DECATRIENAMIDE (SPILANTHOL), AND FOOD OR DRINK, FRAGRANCE OR COSMETIC, OR PHARMACEUTICAL COMPRISING THE SAME

TECHNICAL FIELD

The present invention relates to a production method of spilanthol which is useful as a flavor or fragrance compound and use thereof.

BACKGROUND OF THE INVENTION

It is known that certain substances cause a smarting or numbing stimulus and/or a piercing stimulative feeling. These substances are used in food or drink as general spices and/or herb spices. As substances having these stimulative feelings, jambu oleoresin; spilanthol which is contained in para cress (*Spilanthes* sp.), *spilanthes acmella* and the like; sanshool-I, sanshool-II and sanshoamide contained in zanthoxylum pepperitum; chavicine and piperine contained in a black pepper (*Piper nigrum*), and the like are known. Particularly, (2E,6Z,8E)-N-isobutyl-2,6,8-decatrienamide (spilanthol) is known as an effective component which has a strong anesthetic tingling action, and there are several reports on its synthesis. However, the already reported methods have many problems, such as the necessity of using a highly toxic reagent and an expensive reagent and of employing purification step such as a silica gel column chromatography which is not fit for a large scale production, so that an industrially applicable production method has been in demand for providing it in a large scale.

DISCLOSURE OF THE INVENTION

Problems that the Invention is to Solve

An object of the invention is to provide a method for producing spilanthol in a large scale without using expensive reagents.

Means for Solving the Problems

With the aim of solving the above-mentioned problem, the present inventors have carried out examinations and found as a result an industrially applicable method for producing spilanthol.

That is, the invention relates to the following [1] to [23].

[1] A production method of N-isobutyl-2,6,8-decatrienamide, wherein a column chromatography purification step is not required in all processes.

[2] The production method according to [1], wherein all processes are carried out at a reaction temperature of −20° C. or more.

[3] The production method according to [1] or [2], wherein a chemical purity of the N-isobutyl-2,6,8-decatrienamide is 80% or more, and a content of a 2E,6Z,8E-isomer of the N-isobutyl-2,6,8-decatrienamide is 65% or more.

[4] The production method of N-isobutyl-2,6,8-decatrienamide according to any one of [1] to [3], which comprises:

(AI) preparing a β-hydroxycarboxylic acid ester represented by the formula (A2) by reducing a β-keto ester represented by the formula (A1) (reduction step),

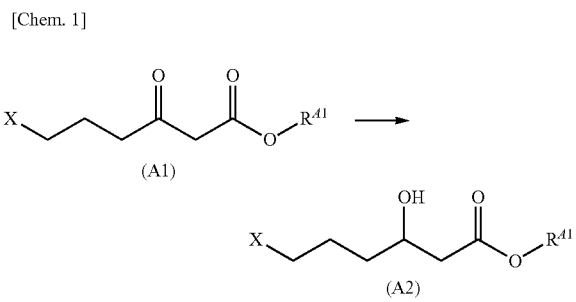

(in the formula (A1) and formula (A2), X represents a chlorine atom or a bromine atom and $R^{A1}$ represents an alkyl group having from 1 to 4 carbon atoms);

(AII) preparing a β-sulfonyloxycarboxylic acid ester represented by the formula (A3) by sulfonic acid esterification of the β-hydroxycarboxylic acid ester represented by the formula (A2) (sulfonic acid esterification step),

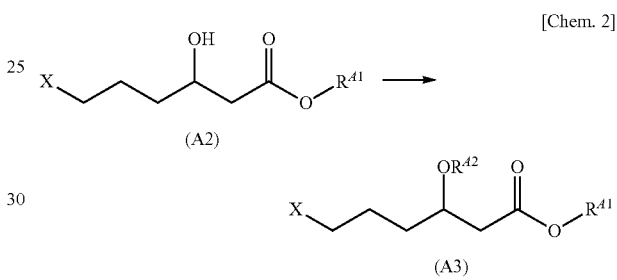

(in the formula (A2), X and $R^{A1}$ are as defined in the foregoing, and in the formula (A3), X represents a chlorine atom or a bromine atom, $R^{A1}$ represents an alkyl group having from 1 to 4 carbon atoms and $R^{A2}$ represents an alkanesulfonyl group, a benzenesulfonyl group or a toluenesulfonyl group);

(AIII) preparing an α,β-unsaturated carboxylic acid ester represented by the formula (A4) from the β-sulfonyloxycarboxylic acid ester represented by the formula (A3) under a basic condition (elimination step),

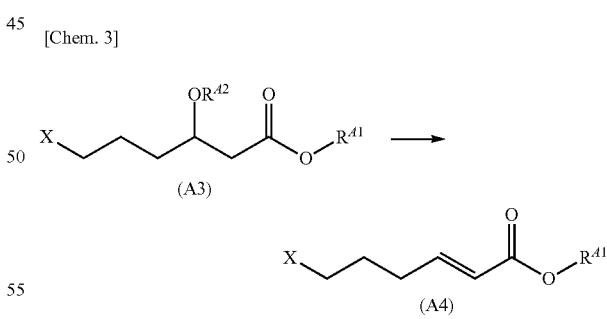

(in the formula (A3), X, $R^{A1}$ and $R^{A2}$ are as defined in the foregoing, and in the formula (A4), X represents a chlorine atom or a bromine atom and $R^{A1}$ represents an alkyl group having from 1 to 4 carbon atoms);

(AIV) preparing a (2E,6Z,8E)-decatrienoic acid ester represented by the formula (A6) by allowing a phosphonium salt represented by the formula (A5), which is derived from the α,β-unsaturated carboxylic acid ester represented by the formula (A4), to react with crotonaldehyde under a basic condition (Wittig reaction step),

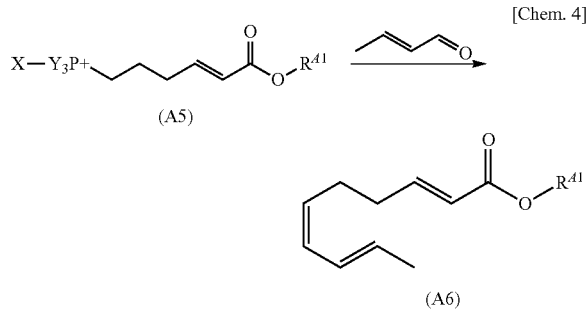

(in the formula (A5), X represents a chlorine atom or a bromine atom, Y represents an alkyl group or an aryl group which may have a substituent group, and $R^{A1}$ represents an alkyl group having from 1 to 4 carbon atoms, and in the formula (A6), $R^{A1}$ represents an alkyl group having from 1 to 4 carbon atoms); and (AV) obtaining (2E,6Z,8E)-N-isobutyl-2,6,8-decatrienamide by allowing the decatrienoic acid ester represented by the formula (A6) to react with isobutylamine in the presence of a catalyst, or by hydrolyzing the decatrienoic acid ester represented by the formula (A6), converting said acid thereafter into an acid halide, and allowing this acid halide to react with isobutylamine (amidation step).

[5] The production method according to [4], wherein the base which is used in the Wittig reaction step of (AIV) is potassium carbonate.

[6] The production method according to [4] or [5], wherein the catalyst which is used in the amidation step of (AV) is lipase.

[7] The production method of N-isobutyl-2,6,8-decatrienamide production method according to any one of [1] to [3], which comprises:

(BI) preparing a hydroxyacetal represented by the formula (B2) by acetalization reaction and hydrolysis of an acyloxybutanal represented by the formula (B1) (acetalization step),

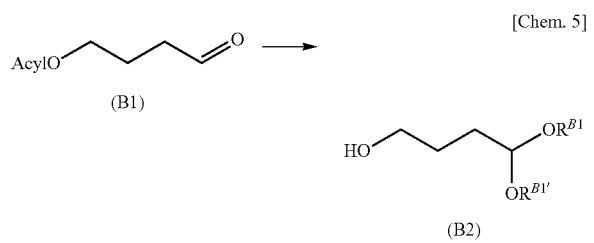

(in the formula (B1), Acyl represents an acyl group having from 2 to 5 carbon atoms, and in the formula (B2), $R^{B1}$ and $R^{B1'}$ each independently represents an alkyl group having from 1 to 4 carbon atoms, or $R^{B1}$ and $R^{B1'}$ may form a divalent carbon chain which may have a substituent group);

(BII) preparing a sulfonic acid ester represented by the formula (B3) (sulfonic acid esterification step),

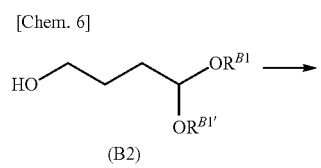

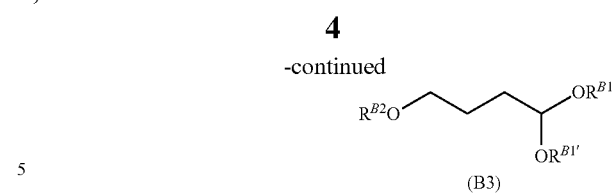

(in the formula (B2), $R^{B1}$ and $R^{B1'}$ are as defined in the foregoing, and in the formula (B3), $R^{B1}$ and $R^{B1'}$ each independently represents an alkyl group having from 1 to 4 carbon atoms, or $R^{B1}$ and $R^{B1'}$ may form a divalent carbon chain which may have a substituent group, and $R^{B2}$ represents an alkanesulfonyl group, a benzenesulfonyl group or a toluenesulfonyl group);

(BIII) preparing a halide represented by the formula (B4) (halogenation step),

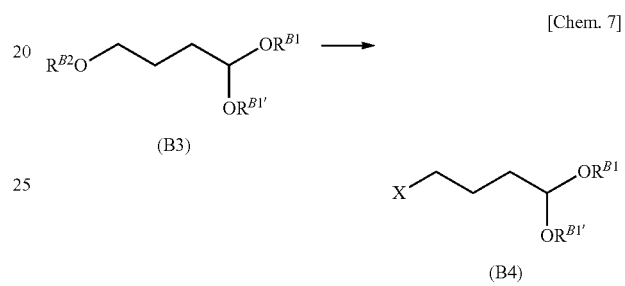

(in the formula (B3), $R^{B1}$, $R^{B1'}$ and $R^{B2}$ are as defined in the foregoing, and in the formula (B4), $R^{B1}$ and $R^{B1'}$ each independently represents an alkyl group having from 1 to 4 carbon atoms, or $R^{B1}$ and $R^{B1'}$ may form a divalent carbon chain which may have a substituent group, and X represents a halogen atom);

(BIV) preparing an acetal of a (4Z,6E)-octadienal represented by the formula (B6) by allowing a phosphonium salt (formula (B5)) which is derived from the formula (B4) to react with crotonaldehyde under a basic condition (Wittig reaction step),

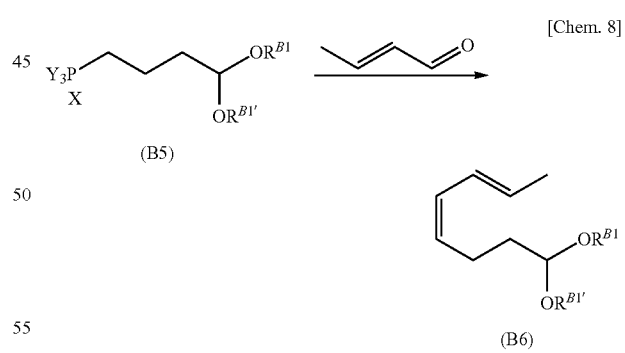

(in the formula (B5), RBI, $R^{B1}$, $R^{B1'}$ and X are as defined in the foregoing and Y represents an alkyl group or an aryl group which may have a substituent group, and in the formula (B6), $R^{B1}$ and $R^{B1'}$ each independently represents an alkyl group having from 1 to 4 carbon atoms, or $R^{B1}$ and $R^{B1'}$ may form a divalent carbon chain which may have a substituent group);

(BV) preparing a (4Z,6E)-octadienal represented by the formula (B7) by deprotecting the octadiene acetal represented by the formula (6) in the presence of an acid catalysis (deprotection step),

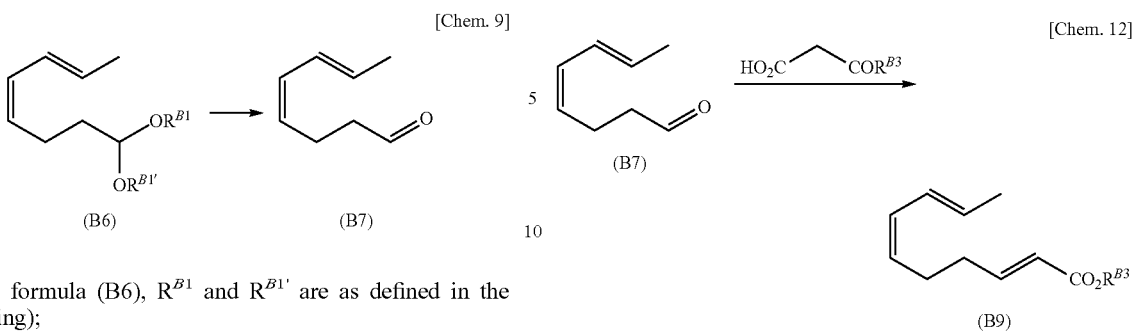

(in the formula (B6), $R^{B1}$ and $R^{B1'}$ are as defined in the foregoing);

(BVI) preparing a mixture of N-isobutyl-2,6,8-decatrienamide and N-isobutyl-3,6,8-decatrienamide represented by the formula (B8), by allowing a (4Z,6E)-octadienal represented by the formula (B7) and malonic acids to undergo condensation under a basic condition,

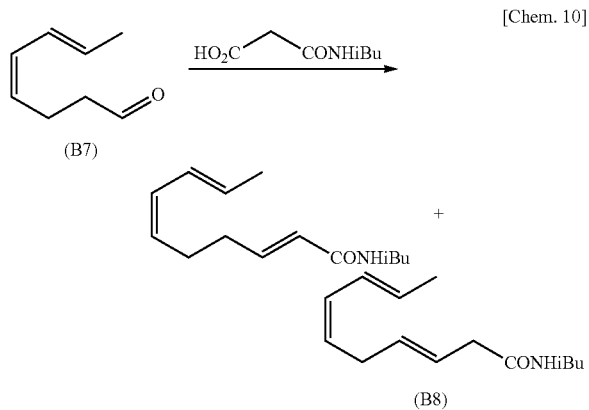

wherein monoisobutyl malonate amide is allowed to undergo the reaction as the malonic acids, (Knoevenagel step 1); and (BVII) isomerizing the N-isobutyl-3,6,8-decatrienamide represented by the formula (B8),

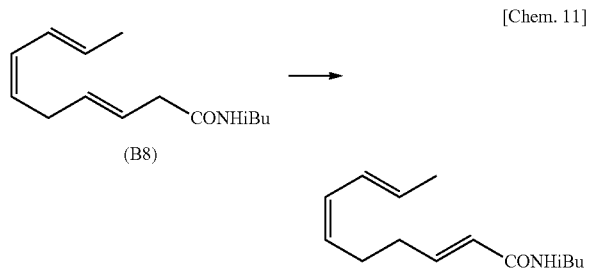

in the mixture of a positional isomer of N-isobutyldecatrienamide obtained in the aforementioned step (VI), into N-isobutyl-2,6,8-decatrienamide (spilanthol) under a basic condition (isomerization step).

[8] The production method according to [7], the method comprising:

preparing a decatrienoic acid ester or decatrienoic acid represented by the formula (B9) by allowing malonic acid or a malonic acid monoester as the malonic acids in the step (BVI) described in [7] under a basic condition (Knoevenagel step 2),

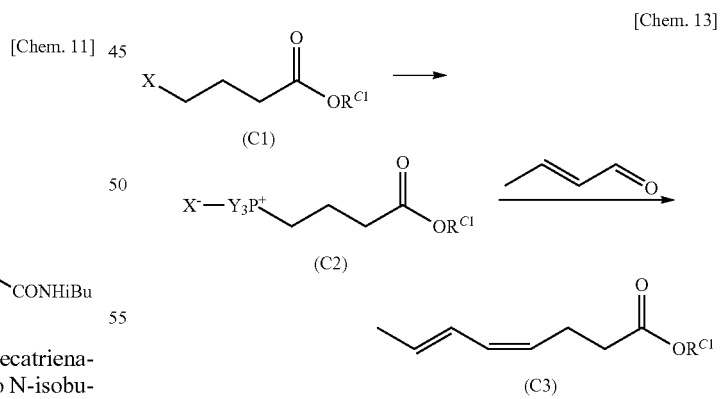

(in the formula (B9), $R^{B3}$ represents a hydrogen atom or an alkyl group having from 1 to 4 carbon atoms); and obtaining (2E,6Z,8E)-N-isobutyl-2,6,8-decatrienamide by allowing the decatrienoic acid ester represented by the formula (B9) to react with isobutylamine in the presence of a catalyst, or by hydrolyzing the decatrienoic acid and decatrienoic acid ester represented by the formula (B9), converting the thus obtained decatrienoic acid into an acid halide and then allowing isobutylamine to act thereon (amidation step).

[9] The production method according to [7] or [8], wherein the base which is used in the Wittig reaction step of the aforementioned step (BIV) is potassium carbonate.

[10] The production method according to [8] or [9], wherein the catalyst which is used in the amidation step is lipase.

[11] The production method of N-isobutyl-2,6,8-decatrienamide according to [1], which comprises:

(CI) preparing a (4Z,6E)-octadienoic acid ester represented by the general formula (C3) by allowing a phosphonium salt represented by the general formula (C2), which is derived from a 4-halobutanoic acid ester represented by the general formula (C1), to react with crotonaldehyde under a basic condition (Wittig reaction step), (in the formulae, $R^{C1}$ is an alkyl group having from 1 to 4 carbon atoms; X is a chlorine atom or a bromine atom; and Y is an alkyl group or an aryl group which may have a substituent group);

(CII) preparing a (4Z,6E)-octadienal represented by the formula (C4) by reducing the (4Z,6E)-octadienoic acid ester represented by the general formula (C3) (reduction step),

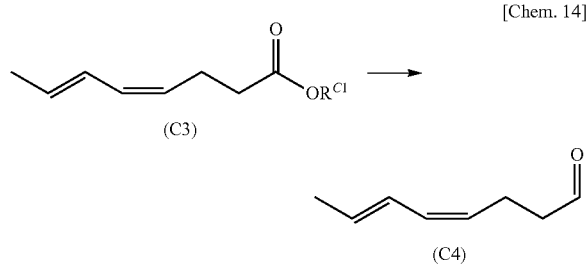

(in the formulae, $R^{C1}$ is as defined in the foregoing);

(CIII) preparing a (2E,6Z,8E)-decatrienoic acid ester represented by the general formula (C6) by allowing the (4Z,6E)-octadienal represented by the formula (C4) to react with a phosphonophosphoric acid ester represented by the general formula (C5) under a basic condition (Wittig reaction),

[Chem. 15]

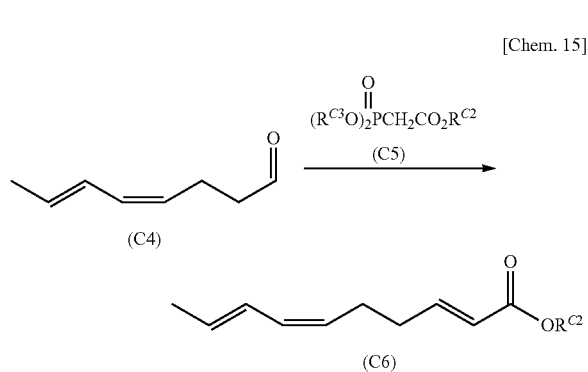

(in the formulae, $R^{C2}$ and $R^{C3}$ are an alkyl group having from 1 to 4 carbon atoms); and (CIV) obtaining (2E,6Z,8E)-N-isobutyl-2,6,8-decatrienamide by allowing the decatrienoic acid ester represented by the general formula (C6) to react with isobutylamine in the presence of a catalyst, or by hydrolyzing the decatrienoic acid ester represented by the general formula (C6), converting said acid thereafter into an acid halide, and allowing this acid halide to react with isobutylamine (amidation step),

[Chem. 16]

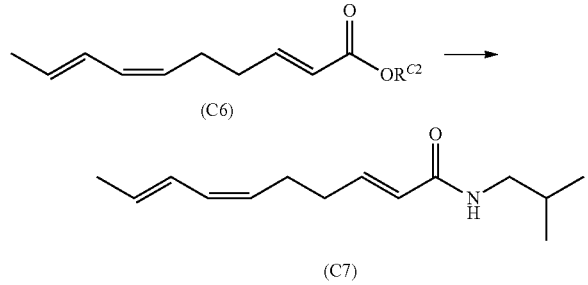

(in the formulae, $R^{C2}$ is as defined in the foregoing).

[12] The production method according to [11], wherein the base which is used in the Wittig reaction step of (CI) and/or (CIII) is potassium carbonate.

[13] The production method according to [11] or [12], wherein the catalyst which is used in the amidation step of (CIV) is lipase.

[14] The production method of N-isobutyl-2,6,8-decatrienamide according to any one of [1] to [3], which comprises:

(DI) preparing a (4Z,6E)-octadienoic acid ester represented by the general formula (D3) by allowing a phosphonium salt represented by the general formula (D2), which is derived from a 4-halobutanoic acid ester represented by the general formula (D1), to react with crotonaldehyde under a basic condition (Wittig reaction step),

[Chem. 17]

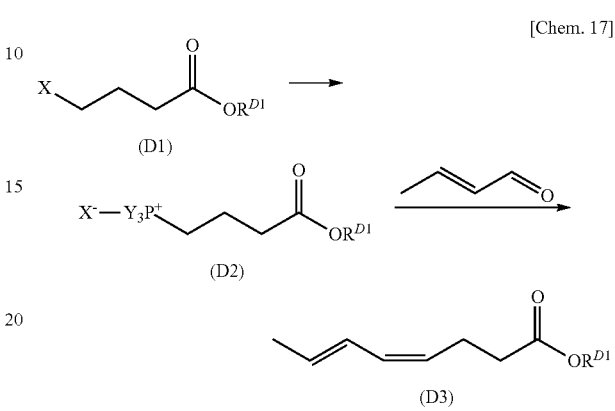

(in the formulae, $R^{D1}$ is an alkyl group having from 1 to 4 carbon atoms; X is a chlorine atom or a bromine atom; and Y is an alkyl group or an aryl group which may have a substituent group);

(DII) preparing (4Z,6E)-octadienoic acid represented by the formula (D4) by hydrolyzing the (4Z,6E)-octadienoic acid ester represented by the general formula (D3) (hydrolysis step),

[Chem. 18]

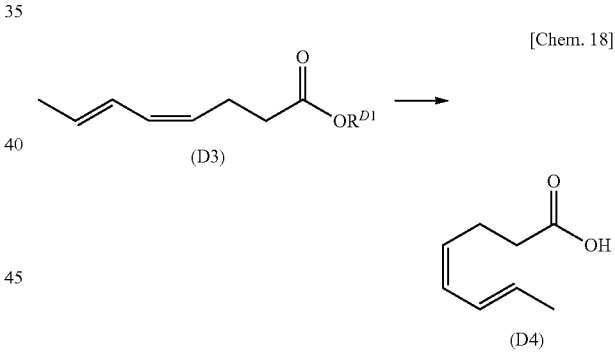

(in the formula, $R^{D1}$ is as defined in the foregoing);

(DIII) preparing a mixed anhydride represented by the general formula (D6) by allowing the 4,6-octadienoic acid represented by the formula (D4) to react with an acid halide represented by the general formula (D5) under a basic condition (mixed anhydride synthesis step),

[Chem. 19]

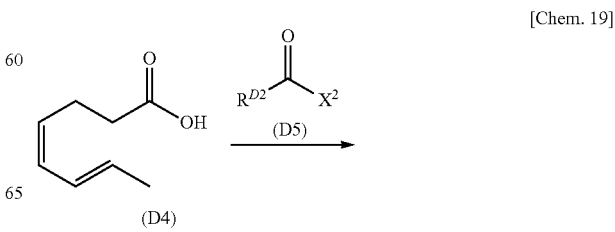

-continued

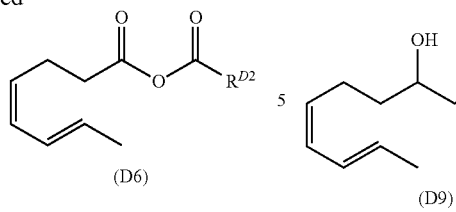

(D6)

(in the formulae, $R^{D2}$ is an alkyl group having from 1 to 4 carbon atoms; and $X^2$ is a chlorine atom or a bromine atom);

(DIV) preparing a 3-oxo-6,8-decadienoic acid ester represented by the general formula (D8) by allowing the mixed anhydride represented by the general formula (D6) to react with a salt of a malonic acid monoester represented by the general formula (D7) (carbon increase step),

[Chem. 20]

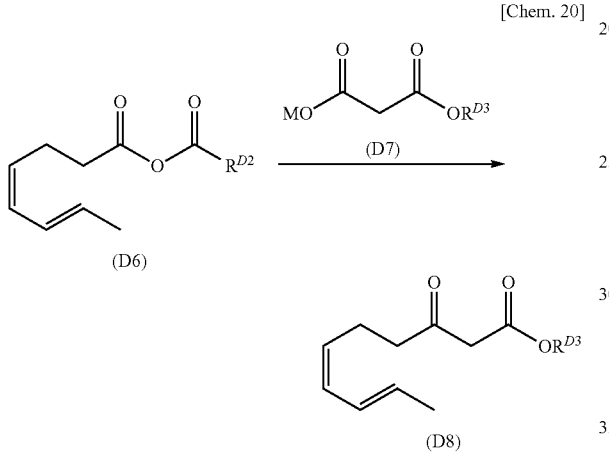

(in the formulae, $R^{D2}$ is as defined in the foregoing; $R^{D3}$ is an alkyl group having from 1 to 4 carbon atoms; and M is sodium or potassium);

(DV) preparing a 3-hydroxy-6,8-decadienoic acid ester represented by the general formula (D9) by reducing a ketone moiety of the 3-oxo-6,8-decadienoic acid ester represented by the general formula (D8) (reduction step),

[Chem. 21]

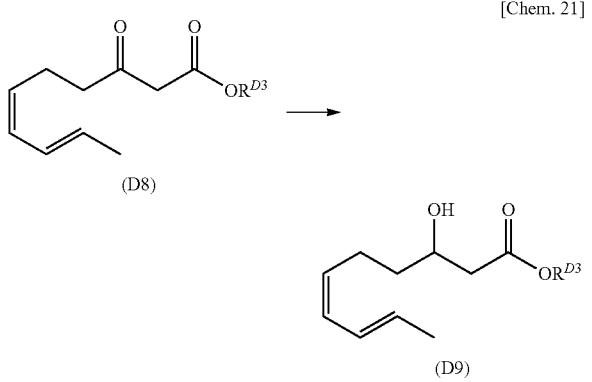

(in the formulae, $R^{D3}$ is as defined in the foregoing);

(DVI) preparing an N-isobutyl-3-hydroxy-6,8-decadienamide represented by the formula (D10) by allowing the 3-hydroxy-6,8-decadienoic acid ester represented by the general formula (D9) to react with isobutylamine (amidation step),

[Chem. 22]

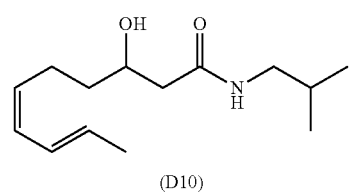

(in the formulae, $R^{D3}$ is as defined in the foregoing);

(DVII) preparing an N-isobutyl-3-sulfonyloxy-6,8-decadienamide represented by the general formula (D11) by subjecting the N-isobutyl-3-hydroxy-6,8-decadienamide represented by the formula (D10) to sulfonic acid esterification (sulfonic acid esterification step),

[Chem. 23]

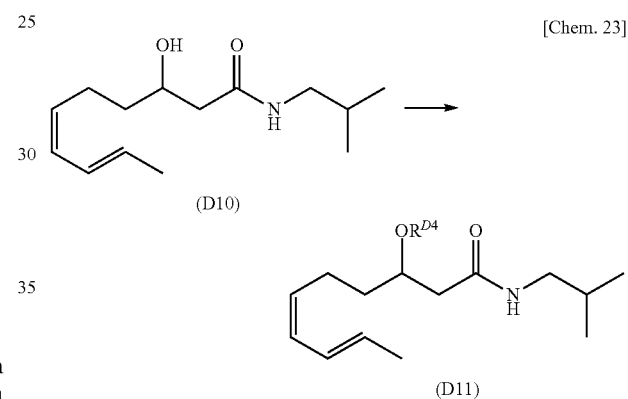

(in the formulae, $R^{D4}$ is an alkanesulfonyl group, a benzenesulfonyl group or a toluenesulfonyl group); and (DVIII) obtaining (2E,6Z,8E)-N-isobutyl-2,6,8-decatrienamide represented by the formula (D12) by treating the N-isobutyl-3-sulfonyloxy-6,8-decadienamide represented by the general formula (D11) with a base under a basic condition (elimination step),

[Chem. 24]

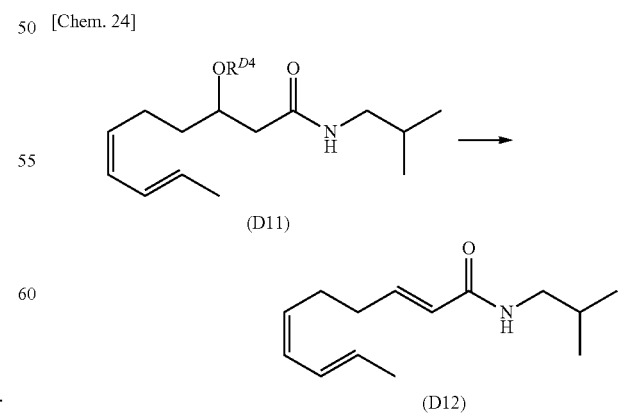

(in the formulae, $R^{D4}$ is as defined in the foregoing).

[15] The production method according to [14], wherein the base which is used in the Wittig reaction step of (DI) is potassium carbonate.

[16] The production method according to [14] or [15], wherein lipase is used as the catalyst in the amidation step of (DVI).

[17] A flavor or fragrance composition, food or drink, fragrance or cosmetic, or pharmaceutical, which comprises the N-isobutyl-2,6,8-decatrienamide which is produced by the method according to any one of [1] to [16].

[18] A β-sulfonyloxycarboxylic acid ester represented by the formula (A3):

[Chem. 25]

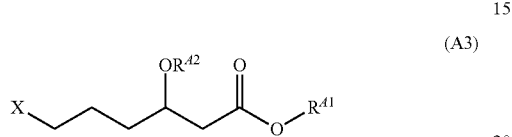

(A3)

(in the formula (A3), X represents a chlorine atom or a bromine atom, $R^{A1}$ represents an alkyl group having from 1 to 4 carbon atoms, and $R^{A2}$ represents an alkanesulfonyl group, a benzenesulfonyl group or a toluenesulfonyl group).

[19] A decatrienoic acid halide represented by the formula (A8):

[Chem. 26]

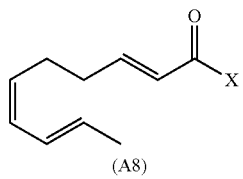

(A8)

(in the formula (A8), X represents a chlorine atom or a bromine atom).

[20] A sulfonate represented by the formula (B3):

[Chem. 27]

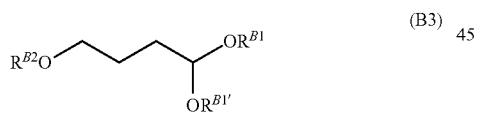

(B3)

(in the formula, $R^{B1}$ and $R^{B1'}$ each independently represent an alkyl group having from 1 to 4 carbon atoms, or $R^{B1}$ and $R^{B1'}$ may form a divalent carbon chain which may have a substituent group, and in the formula, $R^{B2}$ represents an alkanesulfonyl group, a benzenesulfonyl group or a toluenesulfonyl group).

[21] An acetal of octadienal represented by the formula (B6):

[Chem. 28]

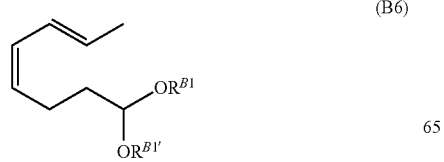

(B6)

(in the formula, $R^{B1}$ and $R^{B1'}$ each independently represent an alkyl group having from 1 to 4 carbon atoms, or $R^{B1}$ and $R^{B1'}$ may form a divalent carbon chain which may have a substituent group).

[22] An N-isobutyl-3-hydroxy-6,8-decadienamide represented by the formula (D10):

[Chem. 29]

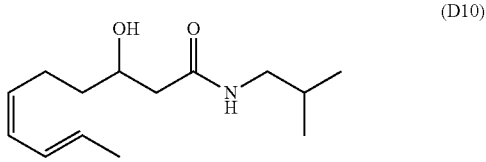

(D10)

[23] An N-isobutyl-3-sulfonyloxy-6,8-decadienamide represented by the formula (D11):

[Chem. 30]

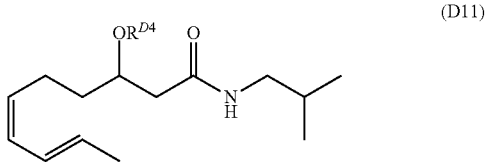

(D11)

(in the formula, $R^{D4}$ is an alkanesulfonyl group, a benzenesulfonyl group or a toluenesulfonyl group).

Advantage of the Invention

It becomes possible by the invention to industrially carry out production of spilanthol without using expensive reagents and without passing through purification step such as a column chromatography. The spilanthol obtained by the invention is useful as a flavor or fragrance component.

BEST MODE FOR CARRYING OUT THE INVENTION

The production method of (2E,6Z,8E)-N-isobutyl-2,6,8-decatrienamide (spilanthol) of the invention does not require a purification step by a column chromatography through the entire steps. In addition, all steps in the production method of the invention are carried out at a reaction temperature of preferably −20° C. or more, more preferably from 0 to 120° C.

As illustrative embodiments of the production method of the invention, the production methods A to D shown in the following can be cited.

<Production Method A>

As an outline, the production method of (2E,6Z,8E)-N-isobutyl-2,6,8-decatrienamide (spilanthol) of the invention is carried out by the reactions which comprise the steps shown in the following.

[Chem. 31]

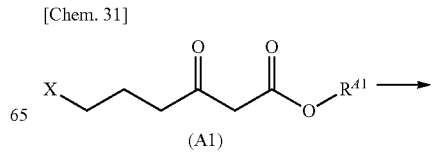

(A1)

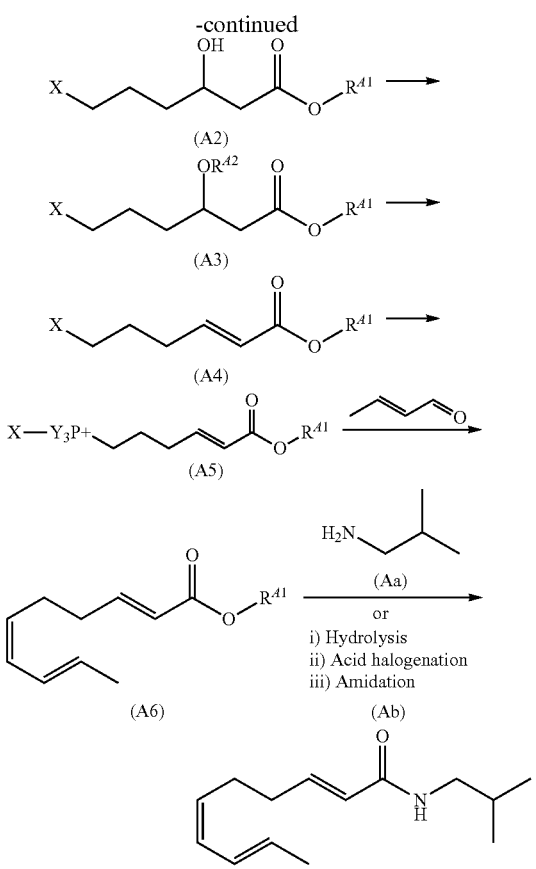

(In the formulae, $R^{41}$ represents an alkyl group having from 1 to 4 carbon atoms, $R^{42}$ represents an alkanesulfonyl group, a benzenesulfonyl group or a toluenesulfonyl group, X represents a chlorine atom or a bromine atom, and Y represents an alkyl group or an aryl group which may have a substituent group.)

That is, (AI) a step for preparing a β-hydroxycarboxylic acid ester represented by the formula (A2) by reducing a β-keto ester represented by the formula (A1) (reduction step);

(AII) a step for preparing a β-sulfonyloxycarboxylic acid ester represented by the formula (A3) by sulfonic acid esterification of the β-hydroxycarboxylic acid ester represented by the formula (A2) (sulfonic acid esterification step);

(AIII) a step for preparing an α,β-unsaturated carboxylic acid ester represented by the formula (A4) from the β-sulfonyloxycarboxylic acid ester represented by the formula (A3) under a basic condition (elimination step);

(AIV) a step for preparing a (2E,6Z,8E)-decatrienoic acid ester represented by the formula (A6) by allowing a phosphonium salt represented by the formula (A5), which is derived from the α,β-unsaturated carboxylic acid ester represented by the formula (A4), to react with crotonaldehyde under a basic condition (Wittig reaction step);

(AV) a step for obtaining (2E,6Z,8E)-N-isobutyl-2,6,8-decatrienamide by allowing the decatrienoic acid ester represented by the formula (A6) to react with isobutylamine in the presence of a catalyst, or by hydrolyzing the decatrienoic acid ester represented by the formula (A6), converting said acid ester thereafter into an acid halide, and allowing this acid halide to react with isobutylamine (amidation step).

A series of these reactions are shown in the aforementioned reaction scheme.

According to the production method A of the invention, the alkyl group having from 1 to 4 carbon atoms means a methyl group, an ethyl group, a propyl group, an isopropyl group, a butyl group, an isobutyl group, a s-butyl group or a t-butyl group.

The reduction step of (AI) in the production method A of the invention is not particularly limited, but a catalytic hydrogenation reaction which uses a homogeneous catalyst or heterogenous catalyst containing transition metal such as ruthenium, palladium and nickel, a hydride reduction by metal hydride such as sodium borohydride, and the like can be used.

Regarding the reaction temperature at this step, it can be carried out at from −20 to 120° C., preferably from 40 to 100° C.

The sulfonic acid esterification step of (AII) in the production method A of the invention can be carried out by allowing a sulfonic acid esterification agent such as methanesulfonyl chloride to react with the β-hydroxycarboxylic acid ester represented by the formula (A2) obtained in the above-mentioned (AI), in the presence of a base. As the sulfonic acid esterification agent, alkanesulfonyl chloride such as methanesulfonyl chloride and ethanesulfonyl chloride, arenesulfonyl chloride such as benzenesulfonyl chloride and p-toluenesulfonyl chloride, and the like can be cited. In this connection, the β-sulfonyloxycarboxylic acid ester represented by the formula (A3), obtained in this step, is a novel compound. Though the base to be used is not particularly limited, triethylamine, tributylamine, pyridine and the like can be preferably cited.

Regarding the reaction temperature at this step, it can be carried out at from −20 to 120° C., preferably from −10 to 50° C.

The elimination step of (AIII) in the production method A of the invention can be carried out by preferably heating the sulfonic acid ester represented by the formula (A3) obtained in the above-mentioned (AII) in the presence of a base. Though the base to be used is not particularly limited, triethylamine, tributylamine, pyridine and the like can be preferably cited.

Regarding the reaction temperature at this step, it can be carried out at from −20 to 120° C., preferably from 40 to 100° C.

The Wittig reaction step of (AIV) in the production method A of the invention can be carried out by allowing the α,β-unsaturated carboxylic acid ester represented by the formula (A4) obtained in the above-mentioned (AIII) to react with a tertiary phosphine to convert into a phosphonium salt, and then allowing crotonaldehyde to act thereon under a basic condition. The base to be used is not particularly limited, but preferably, lithium carbonate, sodium carbonate, calcium carbonate, cesium carbonate, lithium hydroxide, sodium hydroxide, potassium hydroxide, cesium hydroxide, magnesium hydroxide, calcium hydroxide, barium hydroxide and the like can be cited.

Regarding the reaction temperature at this step, it can be carried out at from −20 to 120° C., preferably from 40 to 100° C.

In addition, it is possible to exchange the halogen atom of the compound represented by the formula (A4) with a halogen atom having further high activity for phosphonium salt formation, prior to preparing the phosphonium salt (e.g., from chlorine atom to bromine atom, or vice versa).

As the tertiary phosphine to be used in this case, a compound such as $PY_3$ (Y represents an alkyl group or an aryl group which may have a substituent group) can be cited. As the alkyl group represented by Y, an alkyl group having from 1 to 4 carbon atoms, a pentyl group, a hexyl group, an octyl group, a decyl group, a cyclohexyl group and the like can be cited. Also, as the aryl group of the aryl group which may have a substituent group, as represented by Y, a phenyl group, a naphthyl group and the like can be cited, and as the substituent group, an alkyl group having from 1 to 4 carbon atoms can be cited.

It is possible also to use the target substance in each of the above-mentioned (AI) to (AIV) in the subsequent step as a crude product without carrying out a purification operation, or it can be used in the subsequent step after carrying out a generally used purification operation (distillation, recrystallization and the like).

In this connection, (2E,6Z,8E)-2,6,8-decatrienoic acid chloride and (2E,6Z,8E)-N-isobutyl-2,6,8-decatrienoic acid bromide, represented by the formula (A8), which are intermediates at this step, are novel compounds. In addition, chemical purity and isomer ratio of the thus obtained (2E,6Z,8E)-N-isobutyl-2,6,8-decatrienamide (spilanthol) can be improved by carrying out purification steps such as distillation as occasion demands.

<Production Method B>

As an outline, the method B for producing (2E,6Z,8E)-N-isobutyl-2,6,8-decatrienamide (spilanthol) of the invention is carried out by the reactions which comprise the steps shown in the following.

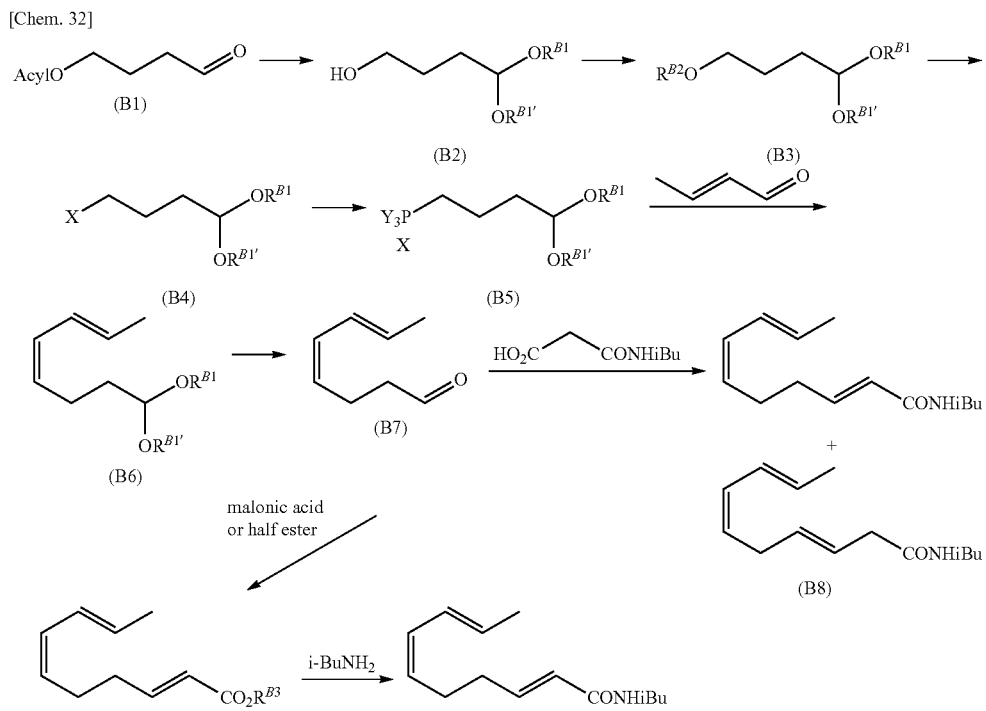

The amidation step of (AV) in the production method A of the invention can be carried out by directly subjecting the decatrienoic acid ester represented by the formula (A6) obtained in the above-mentioned (AIV) to amidation in the presence of a catalyst, or by hydrolyzing the decatrienoic acid ester represented by the formula (A6) to convert into corresponding decatrienoic acid, and then allowing an acid halogenation agent to act thereon to convert into a decatrienoic acid halide, and subjecting said acid halide and isobutylamine to amidation in the presence of a base.

As the catalyst which can be used in this step, a metal compound such as zinc acetate, zinc trifluoroacetate or a cluster compound thereof and an enzyme such as lipase can be cited.

Regarding the reaction temperature at the amidation step by a catalyst, it can be carried out at from −20 to 120° C., preferably from 20 to 80° C.

Regarding the reaction temperature at the amidation step which passes through an acid halide, it can be carried out at from −20 to 120° C., preferably from −10 to 50° C.

(In the formulae, Acyl represents an acyl group having from 2 to 5 carbon atoms, $R^{B1}$ and $R^{B1'}$ each independently represent an alkyl group having from 1 to 4 carbon atoms, or $R^{B1}$ and $R^{B1'}$ may form a divalent carbon chain which may have a substituent group, $R^{B2}$ represents an alkanesulfonyl group, a benzenesulfonyl group or a toluenesulfonyl group, and $R^{B3}$ represents a hydrogen atom or an alkyl group having from 1 to 4 carbon atoms.)

That is, (BI) a step for preparing a hydroxyacetal represented by the formula (B2) by an acetalization reaction and hydrolysis of an acyloxybutanal represented by the formula (B1) (acetalization step);

(BII) a step for preparing a sulfonic acid ester represented by the formula (B3) (sulfonic acid esterification step);

(BIII) a step for preparing a halide represented by the formula (B4) (halogenation step);

(BIV) a step for preparing an acetal of (4Z,6E)-octadienal represented by the formula (B6) by allowing a phosphonium salt (formula (B5)) which is derived from the formula (B4) to react with crotonaldehyde under a basic condition (Wittig reaction step);

(BV) a step for preparing (4Z,6E)-octadienal represented by the formula (B7) by deprotecting the octadiene acetal represented by the formula (6) in the presence of an acid catalysis (deprotection step);

(BVI) a step for preparing a mixture of N-isobutyl-2,6,8-decatrienamide and N-isobutyl-3,6,8-decatrienamide represented by the formula (B8), by allowing the (4Z,6E)-octadienal represented by the formula (B7) and malonic acids to undergo condensation under a basic condition, wherein monoisobutyl malonate amide is allowed to undergo the reaction as the malonic acids, (Knoevenagel step 1); and (BVII) a step for isomerizing the N-isobutyl-3,6,8-decatrienamide represented by the formula (B8), in the mixture of a positional isomer of N-isobutyldecatrienamide obtained in the aforementioned step (VI), into N-isobutyl-2,6,8-decatrienamide (spilanthol) under a basic condition (isomerization step).

A series of these reactions are shown in the aforementioned reaction scheme.

According to the production method B of the invention, the alkyl group having from 1 to 4 carbon atoms means a methyl group, an ethyl group, a propyl group, an isopropyl group, a butyl group, an isobutyl group, a s-butyl group or a t-butyl group.

The acetalization step of (BI) in the production method B of the invention is not particularly limited but can be carried out by a general acetalization reaction of the formyl group of 4-acyloxybutanal, using mono-ol such as methanol and ethanol, diol such as ethylene glycol, orthoformic acid ester such as methyl orthoformate, or the like.

In addition, the de-acylation by hydrolysis after carrying out the acetalization reaction can also be carried out in the usual way, and a corresponding hydroxy form can be obtained. As the acyl group of 4-acyloxybutanal, which is used in this case, acyl groups such as an acetyl group, a propanoyl group and a butyryl group can be cited. In addition, as the divalent carbon chain which is formed by $R^{B1}$ and $R^{B1'}$ and becomes the acetal moiety, a methylene group, an ethylene group, a trimethylene group, a 2,3-butanediyl group and the like can be cited.

Regarding the reaction temperature at this step, it can be carried out at from −10 to 100° C., preferably from 0 to 40° C.

The sulfonic acid esterification step of (BII) in the production method B of the invention can be carried out by allowing sulfonic acid esterification agent such as methanesulfonyl chloride to react with the hydroxyacetal represented by the formula (2) obtained in the above-mentioned (BI), in the presence of a base. As the sulfonic acid esterification agent, alkanesulfonyl chloride such as methanesulfonyl chloride, ethanesulfonyl chloride, arenesulfonyl chloride such as benzenesulfonyl chloride and p-toluenesulfonyl chloride, and the like can be cited. In this connection, the sulfonic acid ester represented by the formula (3) obtained in this step is a novel compound.

Regarding the reaction temperature at this step, it can be carried out at from −10 to 100° C., preferably from 0 to 10° C.

The halogenation step of (BIII) in the production method B of the invention can be carried out by allowing the sulfonic acid ester represented by the formula (3) obtained in the above-mentioned step (BII) to react with alkali metal halide such as lithium bromide.

Regarding the reaction temperature at this step, it can be carried out at from −10 to 100° C., preferably from 0 to 40° C.

The Wittig reaction step of (BIV) in the production method B of the invention can be carried out by allowing the acetal halide represented by the formula (4) obtained in the above-mentioned (BIII) to react with a tertiary phosphine to convert into a phosphonium salt, and then allowing crotonaldehyde to act thereon under a basic condition. As the tertiary phosphine to be used in this case, a compound such as $PY_3$ (Y represents an alkyl group or an aryl group which may have a substituent group) can be cited. As the alkyl group represented by Y, an alkyl group having from 1 to 4 carbon atoms, a pentyl group, a hexyl group, an octyl group, a decyl group, a cyclohexyl group and the like can be cited. Also, as the aryl group of the aryl group which may have a substituent group, as represented by Y, a phenyl group, a naphthyl group and the like can be cited, and as the substituent group, an alkyl group having from 1 to 4 carbon atoms can be cited. In this connection, the acetal of 4Z,6E-octadienal which is obtained in this step is a novel compound.

Regarding the reaction temperature at this step, it can be carried out at from −10 to 100° C., preferably from 30 to 90° C.

The deprotection step of (BV) in the production method B of the invention is not particularly limited and can be carried out by a generally used conversion method of acetal into aldehyde. Regarding the reaction temperature at this step, it can be carried out at from −10 to 100° C., preferably from 50 to 80° C.

The Knoevenagel step 1 of (BVI) in the production method B of the invention can use a general method in which an aldehyde and an active methylene compound are reacted in the presence of a base and is carried out by using 4Z,6E-octadienal as the aldehyde and monoisobutyl malonate amide as the active methylene compound. In this step, two isomers of αβ unsaturated compound and βγ unsaturated compound are formed for the carbonyl group, but the isomerization reaction of the subsequent step can be carried out without separating both isomers.

Regarding the reaction temperature at this step, it can be carried out at from −10 to 100° C., preferably from 30 to 90° C.

In the isomerization reaction step of (BVII) in the production method B of the invention, the βγ unsaturated isomer can be selectively isomerized into αβ unsaturated isomer by heating the mixture of two isomers obtained in the aforementioned step (BVI) in the presence of a base. As the base to be used in this case, an inorganic base is desirable.

Regarding the reaction temperature at this step, it can be carried out at from −10 to 100° C., preferably from 50 to 90° C.

In addition, as shown in the Knoevenagel step 2 (BVIII) of the production method of the invention, decatrienoic acid or an ester thereof as a precursor of spilanthol can be obtained by the use of malonic acid or a malonic acid half ester instead of the monoisobutyl malonate amide which is used in the aforementioned Knoevenagel step 1. As shown in the amidation step (BIX), spilanthol can also be obtained when the thus obtained decatrienoic acid or an ester thereof is hydrolyzed by a general method as occasion demands, and then converted into an acid chloride using an acid chloride forming agent and allowed to react with isobutylamine.

In addition, spilanthol can also be obtained by directly condensing a decatrienoic acid ester and isobutylamine using enzyme such as lipase or metal compound such as zinc acetate and zinc trifluoroacetate as the catalyst.

It is possible also to use the target substance in each of the above-mentioned steps in the subsequent step as a crude product without carrying out a purification operation, or it can be used in the subsequent step after carrying out a generally used purification operation (distillation, recrystallization and the like). However, it is desirable to improve chemical purity and isomer ratio of spilanthol by carrying out purification operations such as distillation as occasion demands.

<Production Method C>

As an outline, the method C for producing (2E,6Z,8E)-N-isobutyl-2,6,8-decatrienamide (spilanthol) of the invention is carried out by the reactions which comprise the steps of (CI) to (CIV) shown in the following.

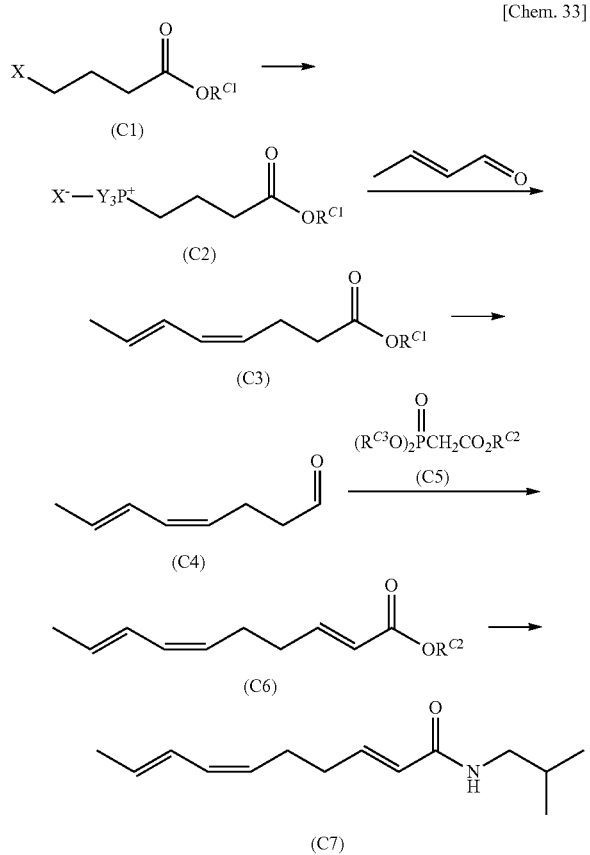

(In the formulae, $R^{C1}$, $R^{C2}$ and $R^{C3}$ are an alkyl group having from 1 to 4 carbon atoms; X is a chlorine atom or a bromine atom; and Y is an alkyl group or an aryl group which may have a substituent group.)

That is, (CI) a step for preparing a (4Z,6E)-octadienoic acid ester represented by the general formula (C3) by allowing a phosphonium salt represented by the general formula (C2), which is derived from a 4-halobutanoic acid ester represented by the general formula (C1) and a tertiary phosphine, to react with crotonaldehyde under a basic condition (Wittig reaction step);

(CII) a step for preparing a (4Z,6E)-octadienal represented by the formula (C4) by reducing the (4Z,6E)-octadienoic acid ester represented by the general formula (C3) (reduction step);

(CIII) a step for preparing a (2E,6Z,8E)-decatrienoic acid ester represented by the general formula (C6) by allowing the (4Z,6E)-octadienal represented by the formula (C4) to react with a phosphonophosphoric acid ester represented by the general formula (C5) under a basic condition (Wittig reaction); and (CIV) a step for obtaining (2E,6Z,8E)-N-isobutyl-2,6,8-decatrienamide by allowing the decatrienoic acid ester represented by the general formula (C6) to react with isobutylamine in the presence of a catalyst, or by hydrolyzing the decatrienoic acid ester represented by the general formula (C6), converting said acid thereafter into an acid halide, and allowing this acid halide to react with isobutylamine (amidation step).

A series of these reactions are shown in the aforementioned reaction scheme.

According to the production method C of the invention, the alkyl group having from 1 to 4 carbon atoms means a methyl group, an ethyl group, a propyl group, an isopropyl group, a butyl group, an isobutyl group, a s-butyl group or a t-butyl group.

The Wittig reaction step of (CI) in the production method C of the invention is not particularly limited and can be carried out by allowing the 4-halobutanoic acid ester represented by the formula (C1) to react with a tertiary phosphine to convert into a phosphonium salt, and then allowing crotonaldehyde to act thereon under a basic condition. In addition, it is possible to exchange the halogen atom of the compound represented by the formula (C1) with a halogen atom having further high activity for phosphonium salt formation, prior to preparing the phosphonium salt (e.g., from chlorine atom to bromine atom, or vice versa). As the tertiary phosphine to be used in this case, a compound such as $PY_3$ (Y represents an alkyl group or an aryl group which may have a substituent group) can be cited. As the alkyl group represented by Y, an alkyl group having from 1 to 4 carbon atoms, a pentyl group, a hexyl group, an octyl group, a decyl group, a cyclohexyl group and the like can be cited. Also, as the aryl group of the aryl group which may have a substituent group, as represented by Y, a phenyl group, a naphthyl group and the like can be cited, and as the substituent group, an alkyl group having from 1 to 4 carbon atoms can be cited.

The reduction step of (CII) in the production method C of the invention is not particularly limited with the proviso that it is a reduction method which can convert an ester into a carboxylic acid, and the (4Z,6E)-octadiene carboxylic acid ester represented by the general formula (C3) obtained in the above-mentioned (CI) can be reduced by using metal hydride such as DIBALH, Red-A1, LTEA or the like can be used.

The Wittig reaction step of (CIII) in the production method C of the invention is not particularly limited and can be carried out by allowing the (4Z,6E)-octadienal represented by the formula (C4) obtained in the above-mentioned (CII) to react with the phosphonophosphoric acid ester represented by the general formula (C5) under a basic condition.

It is possible also to use the target substance in each step of the above-mentioned (CI) to (CIII) in the subsequent step as a crude product without carrying out a purification operation, or it can be used in the subsequent step after carrying out a generally used purification operation (distillation, recrystallization and the like).

The amidation step of (CIV) in the production method C of the invention can be carried out by directly subjecting the decatrienoic acid ester represented by the formula (C6) obtained in the above-mentioned (CIII) and isobutylamine to amidation in the presence of a catalyst, or by hydrolyzing the decatrienoic acid ester represented by the formula (C6) to convert into corresponding decatrienoic acid, and then allowing an acid halogenation agent to act thereon to convert into a decatrienoic acid halide, and subjecting said acid halide and isobutylamine to amidation in the presence of a base. In addition, it is possible to improve chemical purity and isomer ratio of the thus obtained (2E,6Z,8E)-N-isobutyl-2,6,8-decatrienamide (spilanthol) by carrying out purification operations such as distillation as occasion demands.

<Production Method D>

As an outline, the method D for producing (2E,6Z,8E)-N-isobutyl-2,6,8-decatrienamide (spilanthol) of the invention is carried out by the reactions which comprise the steps of (DI) to (DVIII) shown in the following.

[Chem. 34]

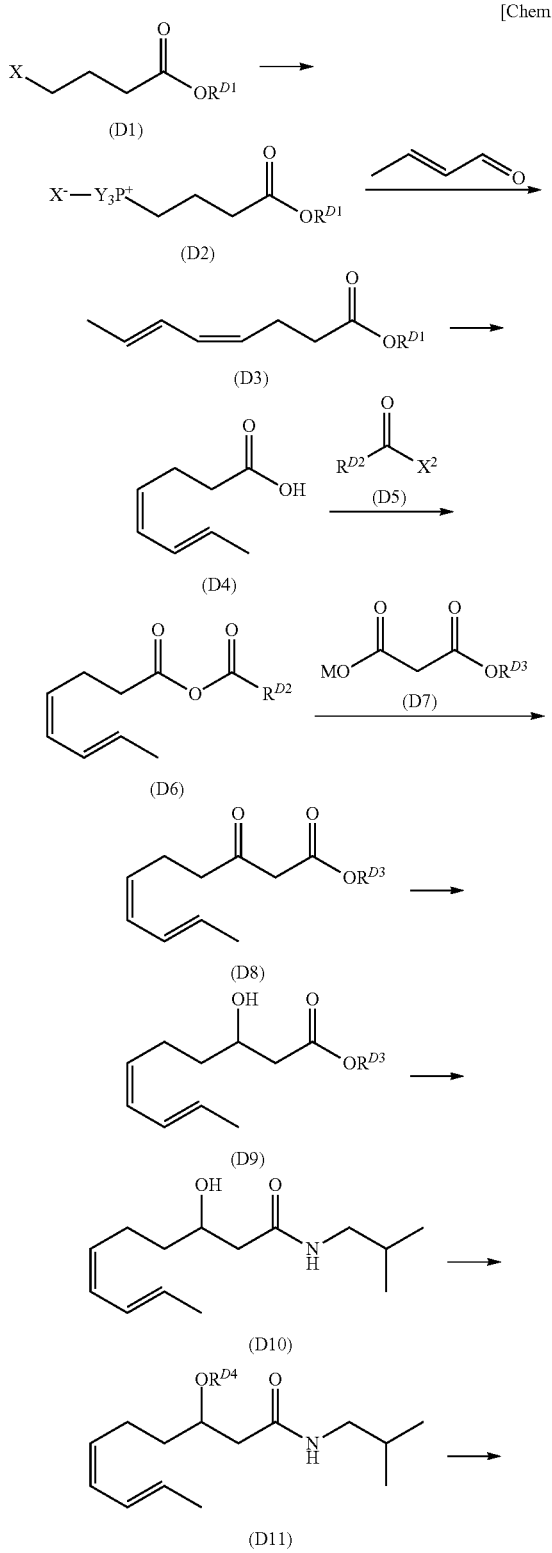

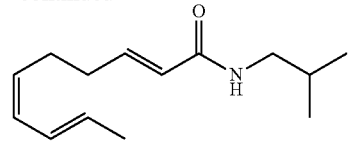

(In the formulae, $R^{D1}$, $R^{D2}$ and $R^{D3}$ are an alkyl group having from 1 to 4 carbon atoms; $R^{D4}$ is an alkanesulfonyl group, a benzenesulfonyl group or a toluenesulfonyl group; $X^1$ and $X^2$ are a chlorine atom or a bromine atom; and Y is an alkyl group or an aryl group which may have a substituent group.)

That is, (DI) a step for preparing a (4Z,6E)-octadienoic acid ester represented by the general formula (D3) by allowing a phosphonium salt represented by the general formula (D2), which is derived from a 4-halobutanoic acid ester represented by the general formula (D1), to react with crotonaldehyde under a basic condition (Wittig reaction step);

(DII) a step for preparing (4Z,6E)-octadienoic acid represented by the formula (D4) by hydrolyzing the (4Z,6E)-octadienoic acid ester represented by the general formula (D3) (hydrolysis step);

(DIII) a step for preparing a mixed anhydride represented by the general formula (D6) by allowing the 4,6-octadienoic acid represented by the formula (D4) to react with an acid halide represented by the general formula (D5) under a basic condition (mixed anhydride synthesis step);

(DIV) a step for preparing a 3-oxo-6,8-decadienoic acid ester represented by the general formula (D8) by allowing the mixed anhydride represented by the general formula (D6) to react with a salt of a malonic acid monoester represented by the general formula (D7) (carbon increase step);

(DV) a step for preparing a 3-hydroxy-6,8-decadienoic acid ester represented by the general formula (D9) by reducing a ketone moiety of the 3-oxo-6,8-decadienoic acid ester represented by the general formula (D8) (reduction step);

(DVI) a step for preparing N-isobutyl-3-hydroxy-6,8-decadienamide represented by the formula (D10) by allowing the 3-hydroxy-6,8-decadienoic acid ester represented by the general formula (D9) to react with isobutylamine (amidation step);

(DVII) a step for preparing N-isobutyl-3-sulfonyloxy-6,8-decadienamide represented by the general formula (D11) by subjecting the N-isobutyl-3-hydroxy-6,8-decadienamide represented by the formula (D10) to sulfonic acid esterification (sulfonic acid esterification step); and (DVIII) a step for obtaining (2E,6Z,8E)-N-isobutyl-2,6,8-decatrienamide represented by the formula (D12) by treating the N-isobutyl-3-sulfonyloxy-6,8-decadienamide represented by the general formula (D11) with a base under a basic condition (elimination step).

A series of these reactions are shown in the aforementioned reaction scheme.

According to the production method D of the invention, the alkyl group having from 1 to 4 carbon atoms means a methyl group, an ethyl group, a propyl group, an isopropyl group, a butyl group, an isobutyl group, a s-butyl group or a t-butyl group.

The Wittig reaction step of (DI) in the production method D of the invention is not particularly limited and can be carried out by allowing the 4-halobutanoic acid ester represented by the general formula (D1) to react with a tertiary phosphine to convert into a phosphonium salt, and then allowing crotonaldehyde to act thereon under a basic condition. In addition, it is possible to exchange the halogen atom of the compound represented by the formula (D1) with a halogen atom having further high activity for phosphonium salt formation, prior to preparing the phosphonium salt (e.g., from chlorine atom to bromine atom, or vice versa). As the tertiary phosphine to be used in this case, a compound such as $PY_3$ (Y represents an alkyl group or an aryl group which may have a substituent group) can be cited. As the alkyl group represented by Y, an alkyl group having from 1 to 4 carbon atoms, a pentyl group, a hexyl group, an octyl group, a decyl group, a cyclohexyl group and the like can be cited. Also, as the aryl group of the aryl group which may have a substituent group, as represented by Y, a phenyl group, a naphthyl group and the like can be cited, and as the substituent group, an alkyl group having from 1 to 4 carbon atoms can be cited. As the base to be used, it is not particularly limited, but preferably, lithium carbonate, sodium carbonate, calcium carbonate, cesium carbonate, lithium hydroxide, sodium hydroxide, potassium hydroxide, cesium hydroxide, magnesium hydroxide, calcium hydroxide, barium hydroxide and the like can be cited.

Regarding the reaction temperature at this step, it can be carried out at from −10 to 100° C., preferably from 70 to 90° C.

The hydrolysis step of (DII) in the production method D of the invention is not particularly limited with the proviso that it is a reduction method which can convert an ester into a carboxylic acid, but a method in which that of the (4Z,6E)-octadienoic acid ester represented by the general formula (D3) obtained in the above-mentioned (DI) is carried out in an organic solvent in the presence of a base, and the like can be used. As the base to be used, it is not particularly limited, but preferably, lithium hydroxide, sodium hydroxide, potassium hydroxide, cesium hydroxide, magnesium hydroxide, calcium hydroxide, barium hydroxide and the like can be cited, and more preferably, potassium hydroxide or sodium hydroxide can be cited.

Regarding the reaction temperature at this step, it can be carried out at from −10 to 100° C., preferably from 20 to 40° C.

The hydrolysis step of (DIII) in the production method D of the invention is not particularly limited with the proviso that it is a reduction method which can convert a carboxylic acid into a mixed anhydride, and a method in which the (4Z,6E)-octadienoic acid represented by the general formula (D4) obtained in the above-mentioned (DII) and the acid halide represented by the general formula (D5) are allowed to undergo the reaction in an organic solvent under a basic condition, and the like can be used. As the base to be used, it is not particularly limited, but preferably, triethylamine, tributylamine, pyridine and the like can be cited.

Regarding the reaction temperature at this step, it can be carried out at from −10 to 100° C., preferably from 0 to 50° C.

The carbon increase step of (DIV) in the production method D of the invention is not particularly limited, and a method in which the mixed anhydride represented by the general formula (D6) obtained in the above-mentioned (DIII) and a salt of the malonic acid monoester represented by the general formula (D7) are allowed to undergo the reaction in an organic solvent under a basic condition, and the like can be used.

Regarding the reaction temperature at this step, it can be carried out at from −10 to 100° C., preferably from 0 to 50° C.

The reduction step of (DV) in the production method D of the invention is not particularly limited, but a method in which a ketone moiety of the 3-oxo-6,8-decadienoic acid ester represented by the general formula (D8) obtained in the above-mentioned (DIV) is subjected to a contact hydrogenation reaction which uses a homogeneous catalyst or heterogenous catalyst containing transition metal such as ruthenium, palladium or nickel, a hydride reduction by metal hydride such as sodium borohydride, or the like can be used.

Regarding the reaction temperature at this step, it can be carried out at from −10 to 100° C., preferably from 0 to 20° C.

The amidation step of (DVI) in the production method D of the invention can be carried out by directly subjecting the 3-hydroxy-6,8-decadienoic acid ester represented by the general formula (D9) obtained in the above-mentioned (DV) and isobutylamine to amidation in the presence of a catalyst, or by hydrolyzing the 3-hydroxy-6,8-decadienoic acid ester represented by the general formula (D6) to convert into the corresponding 3-hydroxy-6,8-decadienoic acid by a general method, and then allowing an acid halogenation agent to act thereon to convert into a 3-hydroxy-6,8-decadienoic acid halide, and subjecting said acid halide and isobutylamine to amidation in the presence of a base. In this connection, the N-isobutyl-3-hydroxy-6,8-decadienamide represented by the formula (D10) obtained in this step is a novel compound.

As the catalyst, an enzyme such as lipase and a metal compound such as zinc acetate or zinc trifluoroacetate can be cited.

Regarding the reaction temperature at the amidation step by a catalyst, it can be carried out at from −10 to 100° C., preferably from 20 to 80° C.

Regarding the reaction temperature at the amidation step which passes through an acid halide, it can be carried out at from −20 to 120° C., preferably from −10 to 50° C.

The sulfonic acid esterification step of (DVII) in the production method D of the invention can be carried out by allowing a sulfonic acid esterification agent such as methanesulfonyl chloride to react with the N-isobutyl-3-hydroxy-6,8-decadienamide represented by the formula (D10) obtained in the above-mentioned (DVI), in the presence of a base. As the sulfonic acid esterification agent, alkanesulfonyl chloride such as methanesulfonyl chloride and ethanesulfonyl chloride, arenesulfonyl chloride such as benzenesulfonyl chloride and p-toluenesulfonyl chloride, and the like can be cited. In this connection, the β-sulfonyloxycarboxylic acid ester represented by the formula (D3) obtained in this step is a novel compound. Though the base to be used is not particularly limited, triethylamine, tributylamine, pyridine and the like can be preferably cited.

Regarding the reaction temperature at this step, it can be carried out at from −10 to 100° C., preferably from 0 to 10° C.

The elimination step of (DVIII) in the production method D of the invention can be carried out by preferably heating the N-isobutyl-3-sulfonyloxy-6,8-decatrienamide represented by the general formula (D11) obtained in the above-mentioned (DVII) in the presence of a base. In addition, chemical purity and isomer ratio of the thus obtained (2E,6Z,8E)-N-isobutyl-2,6,8-decatrienamide (spilanthol) can be improved by carrying out purification steps such as distillation as occasion demands.

Regarding the reaction temperature at this step, it can be carried out at from −10 to 100° C., preferably from 0 to 15° C.

The spilanthol obtained in this manner is useful as a flavor additive agent for food or drink, fragrance or cosmetic, pharmaceutical and the like, by itself or in combination with sense (the sense of taste, skin sensation and the like) stimulants such as existing cooling and warming agent.

As the above-mentioned existing cooling agent, for example, menthol, menthone, camphor, pulegol, isopulegol, cineol, menthe oil, peppermint oil, spearmint oil, eucalyptus oil, 1-methoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxypropane-1-ol, 1-menthyl lactate, menthone glycerin ketal, N-methyl-2,2-isopropylmethyl-3-methylbutanamide, menthyl glyoxylate, mentha oil, peppermint oil, spearmint and the like can be cited, and these can be used alone or by optionally blending two or more of them.

Also, as the warming (hot taste) agent, for example, vanillyl ethyl ether, vanillyl propyl ether, vanillyl butyl ether, vanillin propylene glycol acetal, ethyl vanillin propylene glycol acetal, capsaicin, gingerol, red pepper oil, red pepper oleoresin, ginger oleoresin, vanillyl nonylate amide, jambu oleoresin, Japanese pepper extract, sanshool-I, sanshool-II, sanshoamide, piper nigrum extract, chavicine, piperine and the like can be cited, and these can be used alone or by optionally blending two or more of them.

In this connection, spilanthol may be directly blended in various products such as food or drink, fragrance or cosmetic, and pharmaceutical, but particularly, it is possible also to firstly blend it in a flavor or fragrance composition together with a sense stimulant, and then blend this flavor or fragrance composition in the product.

As the food or drink, for example, drinks such as fruit juices, fruit wines, milk drinks, carbonated drinks, soft drinks and drink preparations; ices such as ice creams, sherbets and ice candies; desserts such as jelly and pudding; Western style confections such as cake, cookie, chocolate and chewing gum; Japanese-style confections such as bean jam bun, sweet beans jelly and uiro; jams; candies; breads; tea drinks or luxury drinks such as green tea, Oolong tea, black tea, persimmon leaf tea, German chamomile tea, low striped bamboo tea, mulberry tea, Houttuynia cordata tea, Pu-erh tea, Mate tea, Rooibos tea, Gymnema tea, guava tea, coffee and cocoa; soups such as Japanese style soup, Western style soup and Chinese soup; flavor condiments; various convenience drinks or foods; various snack foods, and the like can be cited.

As the fragrance or cosmetic, for example, fragrance products such as eau de parfum, eau de toilette and eau de Cologne; foundation cosmetics such as face washing cream, cleansing cream cold cream, massage cream, milky lotion, face lotion, beauty lotion, pack and make remover; finishing cosmetics such as foundation, face powder, solid face powder, talcum powder, lipstick, lip cream, rouge, eye liner, mascara, eye shadow and eye pack; hair cosmetics such as pomade, set lotion, hair oil, hair treatment, hair cream, hair tonic, hair liquid, hair spray, revitalizing hair tonic and hair dye; medicinal cosmetics such as suntan cosmetic, antiperspirant, after shaving lotion and jell, permanent wave preparation, medicinal soap, medicinal shampoo and medicinal skin cosmetic; hair care products such as shampoo, rinse, rinse in shampoo, conditioner, treatment and hair pack; body cleaners such as soap, body soap, body shampoo and hand soap; bathing preparations such as bath preparation (bath salt, bath tablet, bath liquid or the like), foam bath (bubble bath or the like), bath oil (bath perfume, bath capsule or the like), milk bath, bath jelly and bath cube; cleansers; soft finishes;

deodorants or aromatics; repellents; oral preparations such as dental cream, buccal wash and mouth wash; other sundry goods, and the like can be cited.

As the pharmaceutical, for example, skin external preparations such as poultice preparations and ointments, troches, oral medicines and the like can be cited.

Amount of the spilanthol of the invention to be blended by adding to various foods or drinks, fragrances or cosmetics or pharmaceuticals sharply varies depending on an object matter or the like, but it is desirable to set it to a range of generally from 0.00001 to 30% by mass, it is more desirable to set to a range of from 0.0001 to 10% by mass, based on the object matter.

EXAMPLES

The following describes the invention in detail based on examples, but the invention is not limited thereto. In this connection, the following apparatus were used for the measurement of physical properties of the compounds obtained in the following examples.
NMR: DRX 500 (manufactured by Broker)
GC/MS: GCMS-QP 2010 (manufactured by Shimadzu Corporation)
Column: RTX-1 (30 m in length×0.25 mm in inner diameter, 0.25 μm in liquid phase film thickness)
GC purity: GC-14A (manufactured by Shimadzu Corporation)
Column: ChromatoPack CR-4A (manufactured by Shimadzu Corporation)
capillary column DB-1 manufactured by J & W Scientific (30 m in length×0.25 mm in inner diameter, 0.25 μm in liquid phase film thickness)
Temperature condition: column 100° C.×2 minutes→250° C. (10° C./min), injection inlet 300° C., detector 300° C. (FID)

Example A1

(1) Condensation Reaction

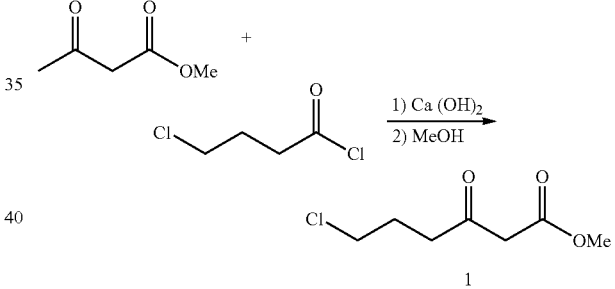

In an atmosphere of nitrogen, methyl acetoacetate (480 g, 4.14 mol), calcium hydroxide (80.0 g, 1.08 mol) and toluene (4822 ml) were added to a 10 liter capacity flask, and dehydration/draining was carried out under toluene reflux. After 1 hour, by cooling to 60° C., 4-chlorobutanoic acid chloride (254 g, 1.8 mol) was added dropwise thereto, followed by stirring at 60° C. Further 1 hour thereafter, methanol (1325 g, 41.4 mol) was added thereto, followed by stirring for 6 hours under methanol reflux. After completion of the reaction, the reaction was stopped with 432 ml (2.16 mol) of 5 N hydrochloric acid, and then the organic layer was separated and the organic layer was washed with 5% sodium carbonate aqueous solution and water. After evaporation of the solvent under a reduced pressure using an evaporator, the residue was distilled under a reduced pressure (75 to 85° C./0.1 ton) to obtain crude 6-chloro-3-oxo-hexanoic acid methyl ester (1); 214.9 g (GC purity; δ 0.3%).

6-Chloro-3-oxo-hexanoic Acid Methyl Ester (1)

GC/MS (m/e); 178 (M$^+$, 2%), 142 (11), 129 (8), 116 (72), 105 (100), 77 (34), 59 (46), 41 (56)
$^1$H-NMR (CDCl$_3$); δ 3.74 (s, 3H), 3.58 (t, 2H, J=6.2 Hz), 3.48 (s, 2H), 2.76 (t, 2H, J=6.9 Hz), 2.09 (tt, 2H, J=6.2, 6.9 Hz)

$^{13}$C-NMR (CDCl$_3$); δ 201.92, 167.83, 52.81, 49.49, 44.47, 40.02, 26.44

(2) Reduction Step

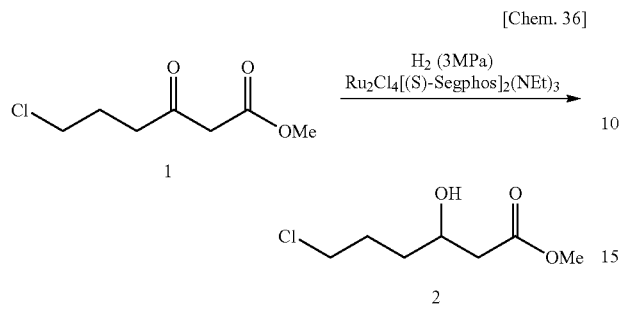

[Chem. 36]

A 214.9 g portion of the above-mentioned crude 6-chloro-3-oxo-hexanoic acid methyl ester (1), Ru$_2$Cl$_4$-[(S)-Segphos]$_2$(NEt)$_3$ (60.7 mg, 0.0725×10$^{-3}$ mol) and methanol (130 ml) were put into a 500 ml capacity autoclave and stirred with hydrogen (3 MPa) at 65 to 70° C. for 6 hours. After completion of the reaction, the solvent was evaporated under a reduced pressure using an evaporator, and then the residue was distilled under a reduced pressure (75 to 85° C./0.1 ton) to obtain 6-chloro-3-hydroxy-hexanoic acid methyl ester (2); 178.2 g {GC purity; 80.1%, pure amount; 142.7 g (0.790 mol, yield 44%/4-chlorobutanoic acid chloride)}.

6-Chloro-3-hydroxy-hexanoic Acid Methyl Ester (2)

GC/MS (m/e); 179 (1%), 162 (1), 147 (1), 127 (3), 113 (15), 103 (100), 71 (68), 61 (28), 43 (84)

$^1$H-NMR (CDCl$_3$); δ 4.04 (m, 1H), 3.72 (s, 3H), 3.60 (m, 2H), 2.53 (dd, 1H, J=3.2, 16.6 Hz), 2.45 (dd, 1H, J=8.9, 16.6 Hz), 1.98 (m, 1H), 1.86 (m, 1H), 1.64 (m, 2H)

$^{13}$C-NMR (CDCl$_3$); δ 173.71, 67.64, 52.21, 45.33, 41.52, 33.96, 29.05

(3) Sulfonic Acid Esterification Step and Elimination Step

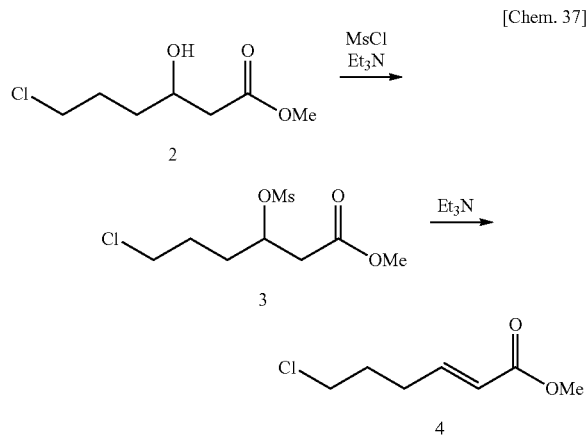

[Chem. 37]

In an atmosphere of nitrogen, 6-chloro-3-hydroxy-hexanoic acid methyl ester (2); 66.5 g {(GC purity; 79.1%, pure amount; 52.6 g (0.295 mol)}, triethylamine (44.7 g, 0.443 mol) and toluene (250 ml) were added to a 500 ml capacity flask, followed by cooling to 5° C. Methanesulfonyl chloride (37.0 g, 0.325 mol) was added dropwise thereto, followed by stirring at 5° C. for 0.5 hour to obtain a toluene solution of 6-chloro-3-methanesulfonyloxy-hexanoic acid methyl ester (3).

Subsequently, triethylamine (44.7 g, 0.443 mol) was further added thereto, followed by stirring for 0.5 hour under triethylamine reflux. After completion of the reaction, water was added thereto to separate the organic layer. After evaporation of the solvent under a reduced pressure using an evaporator, the residue was distilled under a reduced pressure (60 to 70° C./0.1 ton) to obtain 6-chloro-2-hexenoic acid methyl ester (4); 55.7 g {GC purity; 81.4%, pure amount; 45.4 g (0.279 mol, yield 95%/(2)}.

6-Chloro-3-methanesulfonyloxy-hexanoic Acid Methyl Ester (3)

GC/MS (m/e); 227 (1%), 181 (14), 163 (4), 147 (12), 131 (33), 105 (20), 85 (100), 71 (48), 41 (27)

6-Chloro-2-hexenoic Acid Methyl Ester (4)

GC/MS (m/e); 162 (M$^+$, 12%), 131 (44), 113 (100), 81 (20), 67 (32), 55 (28), 41 (38)

$^1$H-NMR (CDCl$_3$); δ 6.94 (dt, 1H, J=15.6, 7.0 Hz) 5.89 (dt, 1H, J=15.6, 1.6 Hz), 3.74 (s, 3H), 3.55 (t, 2H, J=6.4 Hz), 2.39 (ddt, 211, J=1.6, 7.0, 7.2 Hz), 1.95 (tt, 2H J=6.4, 7.2 Hz)

$^{13}$C-NMR (CDCl$_3$); δ 166.79, 147.22, 122.09, 51.46, 43.89, 30.69, 29.18

(4) Bromination

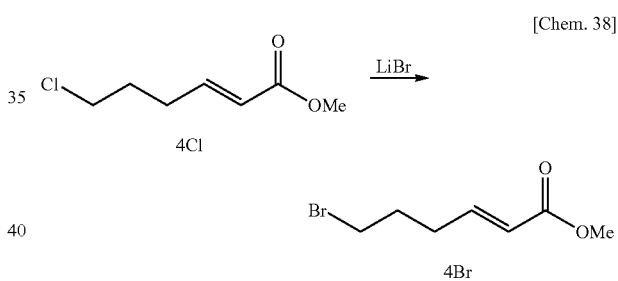

[Chem. 38]

In an atmosphere of nitrogen, 6-chloro-2-hexenoic acid methyl ester (4Cl); 188.8 g {GC purity; 83.6%, pure amount; 157.9 g (0.971 mol)}, lithium bromide (126.5 g, 1.457 mol) and heptane (16 ml) were added to a 500 ml capacity flask, followed by stirring for 6 hours under heptane reflux. After completion of the reaction, heptane was added as an extraction solvent and water was added thereto to separate the organic layer. The solvent was evaporated under a reduced pressure using an evaporator, and then the residue was distilled under a reduced pressure (70 to 80° C./0.1 ton) to obtain 6-bromo-2-hexenoic acid methyl ester (4Br); 203.4 g {GC purity; 82.3%, pure amount (4Br); 167.5 g (0.809 mol, yield 83%/(4Cl)}.

6-Bromo-2-hexenoic Acid Methyl Ester (4Br)

GC/MS (m/e); 208, 206 (M$^+$, 10%), 177 (16), 175 (16), 127 (38), 113 (100), 67 (38), 55 (28), 41 (39)

$^1$H-NMR (CDCl$_3$); δ 6.93 (dt, 11-1, J=15.6, 7.0 Hz), 5.89 (dt, 11-1, J=15.6, 1.6 Hz), 3.74 (s, 3H), 3.42 (t, 2H, J=6.6 Hz), 2.39 (ddt, 2H, J=1.6, 7.0, 7.2 Hz), 2.02 (tt, 2H, J=6.6, 7.2 Hz)

$^{13}$C-NMR (CDCl$_3$); δ 166.77, 147.02, 122.17, 51.47, 32.47, 30.77, 30.42

(5) Wittig Reaction Step

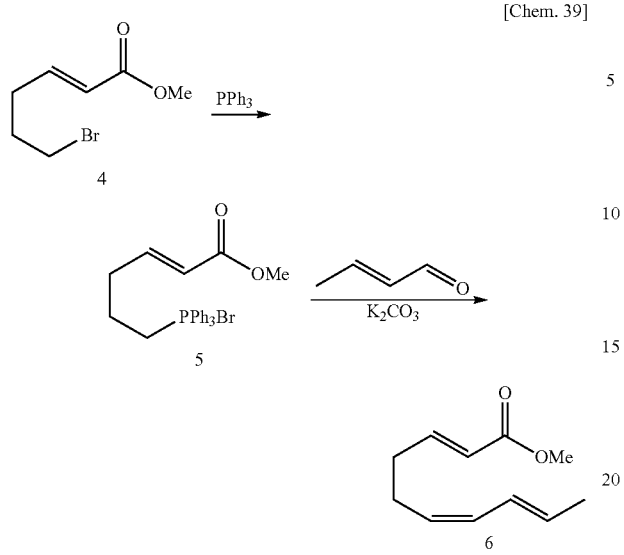

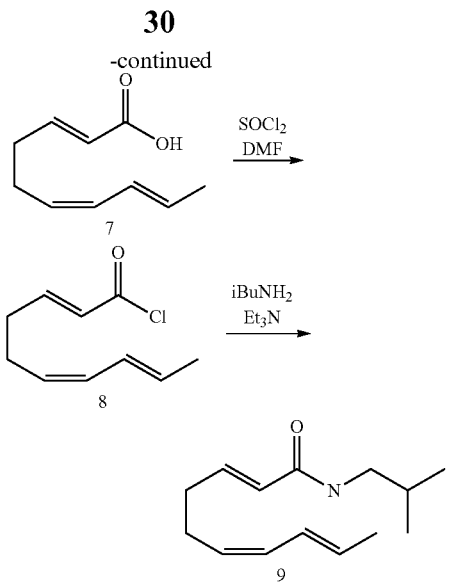

In an atmosphere of nitrogen, 6-bromo-2-hexenoic acid methyl ester (4); 203.4 g {GC purity; 82.3%, pure amount; 167.5 g (0.809 mol)}, triphenylphosphine (254.5 g, 0.970 mol) and acetonitrile (167 ml) were added to a 1 liter capacity flask, followed by stirring at 90° C. for 18 hours. After completion of the reaction, toluene (1900 ml) was added thereto to obtain a toluene solution of a phosphonium salt (5).

After subsequently cooling to 65° C., potassium carbonate (335.3 g, 2.426 mol) and crotonaldehyde (169.8 g, 2.426 mol) were added thereto, followed by stirring at 65° C. for 6 hours. After completion of the reaction, hydrous methanol was added thereto and the organic layer was separated. The solvent was evaporated under a reduced pressure using an evaporator, and then the residue was distilled under a reduced pressure (70 to 80° C./0.1 ton) to obtain 2,6,8-decatrienoic acid methyl ester (6); 138.2 g {GC; 81.2%, pure amount; 112.2 g (0.623 mol, yield 82%/(4))}.

2,6,8-Decatrienoic Acid Methyl Ester (6)

GC/MS (m/e); 180 (M+, 7%), 148 (7), 121 (6), 100 (24), 81 (100), 68 (8), 53 (23), 41 (22)

$^1$H-NMR (CDCl$_3$); δ 6.98 (dt, 1H, J=15.7, 6.6 Hz), 6.28 (m, 1H), 5.98 (dd, 1H, J=10.9 Hz), 5.91 (d, 1H, J=15.7 Hz), 5.70 (m, 1H), 5.25 (m, 1H), 3.73 (s, 3H), 2.2-2.4 (m, 4H), 1.78 (d, 3H, J=6.8 Hz)

$^{13}$C-NMR (CDCl$_3$); δ 167.01, 148.63, 130.09, 129.65, 127.22, 126.60, 121.30, 51.38, 32.27, 26.11, 18.27

(6) Amidation Step

[Chem. 40]

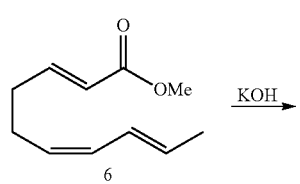

In an atmosphere of nitrogen, 2,6,8-decatrienoic acid methyl ester (6); 19.1 g {GC; 93.9%, pure amount; 17.9 g (0.0995 mol)} and 5 mol/l of potassium hydroxide aqueous solution (60 ml, 0.30 mol) were added to a 200 ml capacity flask, followed by stirring at 70° C. for 2 hours. After completion of the reaction, the reaction was stopped with 5 mol/l of hydrochloric acid (63 ml, 0.315 mol), and then extraction with toluene (32 ml) was carried out to obtain a toluene solution of 2,6,8-decatrienoic acid (7).

In an atmosphere of nitrogen, a toluene solution of the above-mentioned 2,6,8-decatrienoic acid (7) and DMF (3.7 g, 0.05 mol) were added to a 100 ml capacity flask, followed by cooling to 5° C. Thionyl chloride (11.9 g, 0.10 mol) was added dropwise to this, followed by stirring at 5° C. for 0.5 hour to obtain a toluene solution of 2,6,8-decatrienoic acid chloride (8).

In an atmosphere of nitrogen, isobutylamine (7.3 g, 0.10 mol), triethylamine (10.1 g, 0.10 mol) and toluene (32 ml) were added to a 200 ml capacity flask, followed by cooling to 5° C. Subsequently, the toluene solution of 2,6,8-decatrienoic acid chloride (8) obtained in the above was added dropwise thereto, and stirring was carried out at 5° C. for 0.5 hour. After completion of the reaction, the reaction was stopped by adding water, and then the organic layer was separated and the organic layer was washed with 5% sodium carbonate aqueous solution, 0.1 mol/l sodium hydroxide aqueous solution and water in this order. The solvent was evaporated under a reduced pressure using an evaporator, and the residue was distilled under a reduced pressure (130 to 135° C./0.1 torr) to obtain spilanthol (9); 19.7 g {GC purity; 91.2%, pure amount; 18.0 g (0.0817 mol, yield 82%/(6))}.

2,6,8-Decatrienoic Acid (7)

GC/MS (m/e); 166 (M+, 8%), 148 (2), 121 (2), 105 (2), 91 (4), 81 (100), 65 (5), 53 (18), 41 (16)

2,6,8-Decatrienoic Acid Chloride (8)

GC/MS (m/e); 184 (M+, 6%), 149 (7), 121 (3), 105 (2), 93 (3), 81 (100), 68 (14), 53 (15), 41 (14)

Spilanthol (9)

GC/MS (m/e); 221 (M+, 10%), 206 (3), 192 (4), 178 (2), 167 (2), 141 (70), 126 (44), 98 (30), 81 (100), 69 (15), 53 (17), 41 (24)

¹H-NMR (CDCl₃); δ 6.82 (dt, 1H, J=15.3, 6.7 Hz), 6.28 (dd, 1H, J=10.7, 15.0 Hz), 5.97 (dd, 1H, J=10.7, 10.7 Hz), 5.87 (bs, 1H), 5.85 (d, 1H, J=15.3 Hz), 5.69 (dq, 1H, J=15.0, 6.7 Hz), 5.26 (dt, 1H, J=10.7, 6.8 Hz), 3.14 (dd, 2H, J=6.8, 6.8 Hz), 2.31 (dt, 2H, J=6.8, 6.8 Hz), 2.26 (dt, 2H, J=6.7, 6.8 Hz), 1.81 (dq, 1H, J=6.8, 6.8 Hz), 1.77 (d, 3H, J=6.7 Hz), 0.92 (d, 6H, J=6.7 Hz)

¹³C-NMR (CDCl₃); δ 166.45, 143.74, 130.29, 129.83, 128.03, 127.09, 124.65, 47.26, 32.50, 28.97, 26.79, 20.53, 18.67

Example A2

Isobutyl Amidation by Enzyme

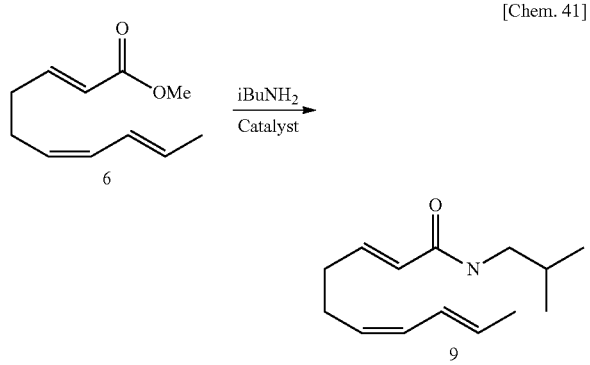

[Chem. 41]

The 2,6,8-decatrienoic acid methyl ester (6); 10 g {GC purity; 96%, pure amount; 8.3 g (0.046 mol), GC purity of (2E,6Z,8E)-form 82.9%} prepared in Example A1, isobutylamine (4.0 g, 0.055 mol), Novozym 435 (5 g) and diisopropyl ether (10 ml) were added to a 50 ml capacity flask and stirring was carried out at 35° C. for 4 days. After completion of the reaction, the enzyme was filtered and then the solvent was evaporated under a reduced pressure using an evaporator, followed by distillation purification, thereby obtaining spilanthol (9); 11.1 g (GC purity of the (2E,6Z,8E)-form: 85.7%).

Example B1

Synthesis of Spilanthol (1) Acetalization Reaction

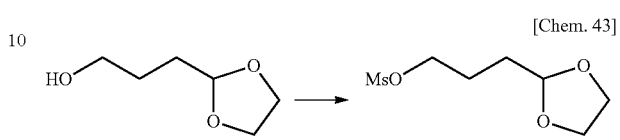

[Chem. 42]

232 g (1.78 mol) of acetoxybutanal was put into a 1 liter capacity four neck distillation flask, and 109 ml (1.1 eq) of ethylene glycol was added thereto under ice-cooling at 5° C. Next, 1.10 g (0.5% wt) of p-toluenesulfonic acid hydrate was added thereto, followed by stirring at room temperature. By heating to 40° C. 1.5 hours thereafter, dehydration reaction was carried out under a reduced pressure, followed by stirring at the same temperature. Two hours thereafter, 232 ml of water and 78.4 g (1.1 eq) of NaOH were added thereto under ice-cooling, followed by stirring for 3 hours, and then 1160 ml of ethyl acetate was added thereto and the organic layer was separated. By subjecting the thus obtained organic layer to solvent evaporation under a reduced pressure, 224 g of the target acetal compound was obtained (yield 95%).

(2) Sulfonic Acid Esterification Reaction

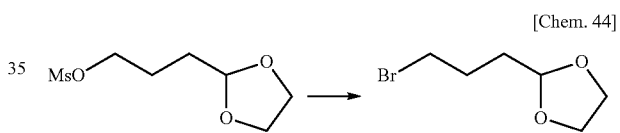

[Chem. 43]

158 g (1.2 mol) of the hydroxyacetal compound obtained in the above-mentioned (1) and 183 ml (1 eq) of triethylamine were dissolved in 790 ml of toluene, and 93 ml (1 eq) of methanesulfonyl chloride was added dropwise thereto under ice-cooling, by spending 2 hours. After completion of the dropwise addition and subsequent 1 hour of stirring at the same temperature, 300 ml of water was added thereto, and the organic layer was separated (pH=9) and then washed three times with 300 ml of water (pH=9). By subjecting the thus obtained organic layer to solvent evaporation under a reduced pressure, 205 g (yield 81%) of the target methanesulfonic acid ester (Ms compound) was obtained.

GC/MS (m/e): 209 (M-H), 113 (M-O₃SMe), 84.73

(3) Bromination reaction

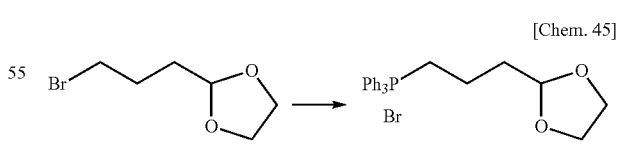

[Chem. 44]

205 g (978 mmol) of the Ms compound obtained in the above-mentioned (2) was dissolved in 410 ml of dimethyl sulfoxide (DMSO), and 84.7 g (1 eq) of LiBr was added thereto at room temperature. After stirring the reaction liquid at 35° C. for 22 hours, 400 ml of toluene and 400 ml of water (s/s=2) were added thereto, and the organic layer was separated, followed by washing with 200 ml of water again. By subjecting the thus obtained organic layer to solvent evaporation under a reduced pressure, 163 g (yield 86%) of the target bromination compound was obtained.

(4) Synthesis of Phosphonium Salt

[Chem. 45]

163 g (836 mmol) of the bromination compound obtained in the above-mentioned (3) and 241 g (1 eq) of triphenylphosphine were dissolved in 163 ml of acetonitrile, followed by stirring at 90° C. for 18 hours, and then the reaction liquid was added to 489 ml of toluene at the same temperature. Crystals were immediately precipitated, followed by cooling to room temperature spontaneously, and filtering and drying to obtain 256 g (yield 67%) of the target phosphonium salt.

(5) Wittig Reaction

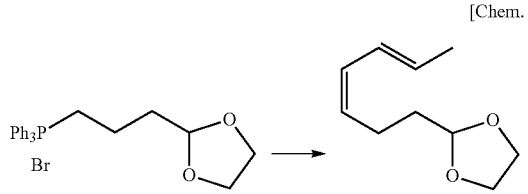

[Chem. 46]

100 g (218.6 mmol) of the phosphonium salt obtained in the above-mentioned (4) and 60.4 g (2 eq) of $K_2CO_3$ were suspended in 500 ml of toluene and 50 ml of DMSO, and 73 ml (4 eq) of crotonaldehyde was added thereto, followed by stirring at 80° C. for 24 hours. The organic layer was separated and washed twice with 200 ml of water, and then 100 ml of $(BuO)_3PO$ was added thereto, followed by evaporation of solvent distillation and distillation under a reduced pressure by Vigreux distillation (60 to 70° C./1 ton), thereby obtaining 32.3 g of the target diene compound (yield 88%, isomer ratio E:Z=16:84, GC purity 73.1%).

GC/MS (m/e): 167 (M-H), 153, 139, 125, 99, 73

(6) Deprotection

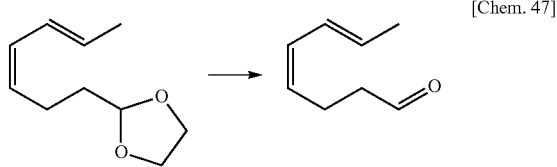

[Chem. 47]

57 g (338.8 mmol) of the diene compound obtained in the above-mentioned (5) was suspended in 114 ml of water, and 114 ml of 50% glyoxylic acid aqueous solution was added thereto, followed by stirring at 70° C. for 3 hours. After separation of the organic layer, 114 ml of water, and 114 ml of 50% glyoxylic acid aqueous solution was added to the organic layer and, followed by stirring at 70° C. for 3 hours. 114 ml of heptane and 57 ml of 5% $Na_2CO_3$ aqueous solution ere added to the reaction liquid and the organic layer was separated, the organic layer was separated and washed twice with 57 ml of water, and then evaporation of solvent and distillation by Vigreux distillation (40 to 50° C./2 ton) were carried out to obtain 32.7 g of the target diene aldehyde compound (yield 78%).

(7) Knoevenagel Step 1

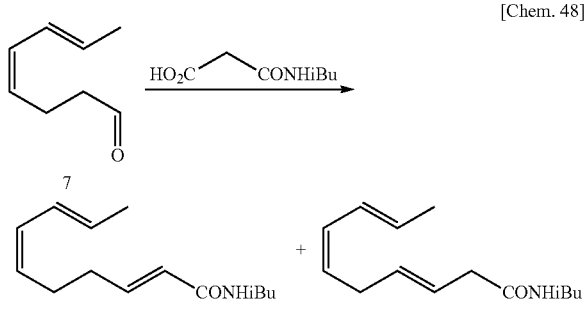

[Chem. 48]

20.7 g (97.5 mmol, 1.1 eq) of monoisobutyl malonate amide, 1.08 g (0.1 eq) of 4-N,N-dimethylamino-pyridine (DMAP) and 0.88 ml (0.1 eq) of piperidine were suspended in 22 ml of toluene and 11 ml of pyridine, followed by stirring at 80° C., and 11 g of the diene aldehyde compound obtained in the above-mentioned (6) was added dropwise to this by spending 30 minutes. After completion of the dropwise addition and subsequent 2 hours of stirring at the same temperature and cooling to room temperature, the organic layer was separated by adding 22 ml of water (pH=8), washed twice with 10% sulfuric acid aqueous solution, washed with water, washed with 5% $Na_2CO_3$ aqueous solution and then finally washed twice with water, and the solvent was evaporated under a reduced pressure to obtain 18.4 g of the target spilanthol mixture (yield 94%, αβ unsaturated form (spilanthol):βγ unsaturated form (8)=43:57).

(8) Isomerization Reaction

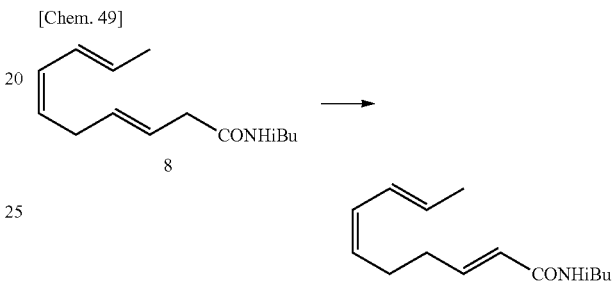

[Chem. 49]

0.05 g (10% wt) of $K_3PO_4$ and 0.05 g (10% wt) of polyethylene glycol (PEG 400) were added to 0.5 g of the spilanthol mixture (αβ unsaturated form:βγ unsaturated form=43:57) obtained in the above-mentioned (7), followed by stirring at 80° C. for 16 hours. When verified by GC, the ratio of αβ unsaturated form to βγ unsaturated form was converted to αβ unsaturated form:βγ unsaturated form=99:1. After cooling of the reaction liquid and subsequent separation of liquid by adding 5 ml of toluene and 5 ml of water, the organic layer was subjected to solvent evaporation under a reduced pressure to obtain 0.5 g of the target spilanthol (yield 99%, αβ unsaturated form:βγ unsaturated form=99:1).

Example B2

Synthesis of Spilanthol (1) Knoevenagel Reaction 2

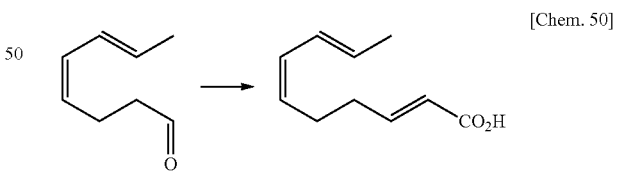

[Chem. 50]

25.1 g (240 mmol, 1.1 eq) of malonic acid, 2.7 g (0.1 eq) of DMAP and 2.2 ml (0.1 eq) of piperidine were suspended in 57 ml of toluene and 27 ml of pyridine, followed by stirring at 70° C., and 27.2 g of the diene aldehyde compound was added dropwise to this by spending 10 minutes. After completion of the dropwise addition and subsequent 2 hours of stirring at the same temperature and cooling to room temperature, the organic layer was separated by adding 82 ml of 6 N HCl (pH=1) and then washed twice with water, and the organic layer was subjected to solvent evaporation under a reduced pressure to obtain 30.2 g of the target triene carboxylic acid (yield 93%).

(2) Amidation Reaction

[Chem. 51]

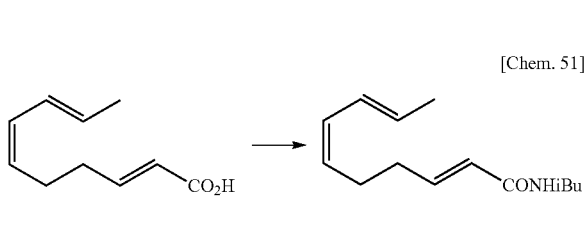

30.2 g (180.5 mmol) of the triene carboxylic acid obtained in the above-mentioned Example B2(1) was dissolved in 90 ml of heptane and 12 ml of dimethylformamide (DMF), and 14.5 ml (1.1 eq) of thionyl chloride was added dropwise thereto by spending 1 hour, while stirring under ice-cooling. After completion of the dropwise addition and subsequent 1 hour of stirring, separation of liquid was carried out by adding 60 ml of water. A heptane solution of the thus obtained acid chloride was added dropwise to a mixture of 60 ml of toluene, 21.5 ml (1.2 eq) of isobutylamine and 30.2 ml (1.2 eq) of triethylamine, by spending 2 hours under ice-cooling, and after completion of the dropwise addition, stirring was carried out at room temperature for 2 hours. The organic layer was separated by adding 120 ml of water, and the organic layer was washed with 120 ml of 0.1 N NaOH aqueous solution and then washed twice with 120 ml of water. By subjecting the thus obtained organic layer to solvent evaporation under a reduced pressure, 35.3 g of the target spilanthol (yield 88%)

Example B3

Isobutyl Amidation by Lipase

[Chem. 52]

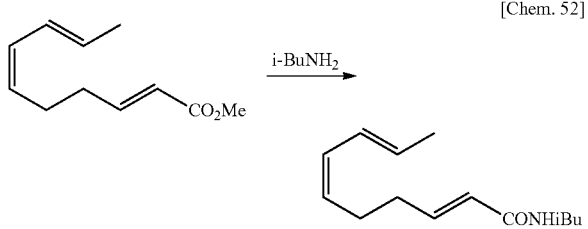

The 2,6,8-decatrienoic acid methyl ester (6) prepared in Example B1; 10 g {GC purity; 96%, pure amount; 8.3 g (0.046 mol), (GC purity of (2E,6Z,8E)-form; 82.9%}, isobutylamine (4.0 g, 0.055 mol), Novozym 435 (5 g) and diisopropyl ether (10 ml) were added to a 50 ml capacity flask, and stirring was carried out at 35° C. for 4 days. After completion of the reaction and subsequent filtration of the enzyme, the solvent was evaporated under a reduced pressure, and distillation purification (130 to 135° C./0.1 ton) was carried out to obtain spilanthol (9); 11.1 g (GC purity of (2E,6Z,8E)-form; 85.7%).

Example C1

(1) Wittig Reaction Step

[Chem. 53]

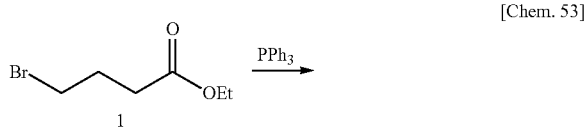

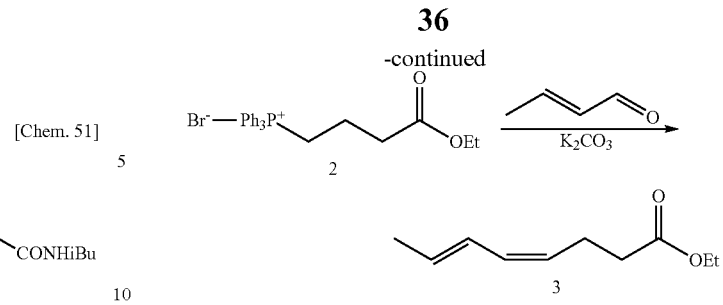

In a stream of nitrogen, ethyl 4-bromobutanoate (1) (195 g, 1.0 mol), triphenylphosphine (288 g, 1.1 mol) and acetonitrile (195 ml) were put into a 1 liter capacity flask equipped with a reflux condenser, a stirrer and a thermometer, followed by heating to 90° C. and stirring for 40 hours. When the reaction solution was added dropwise to toluene (800 ml) and cooled to 20° C., a white solid was precipitated. This solid was filtered and then drying under a reduced pressure was carried out (50° C./1 torr) to obtain a phosphonium salt (2) (420 g, 0.92 mol, yield 92%).
Ethyl 4-triphenylphosphoniumbutanoate bromide (2)
$^1$H-NMR (CDCl$_3$): δ 1.23 (t, 3H, J=7.2), 1.90-1.97 (m, 2H), 2.87 (t, 2H, J=6.3), 3.94-4.04 (m, 2H), 4.10 (q, 2H, J=7.2), 7.63-7.91 (m, 15H)
$^{31}$P-NMR (CDCl$_3$): δ 24.04

In a stream of nitrogen, the phosphonium salt (2) (420 g, 0.92 mol), toluene (1600 ml), potassium carbonate (506.2 g, 3.66 mol) and crotonaldehyde (256.7 g, 3.66 mol) were put into a 5 liter capacity flask equipped with a stirrer and a thermometer, followed by heating to 65° C. and stirring was continued for 7 hours. The reaction solution was cooled to room temperature, mixed with water (840 g), followed by stirring for 30 minutes and then subjecting to separation of liquid. When the solvent of the organic layer was evaporated under a reduced pressure, a solid was precipitated, and the solid was removed by filtration. By distilling this solution under a reduced pressure (65 to 70° C./1.5 ton), ethyl (4Z, 6E)-octadienoate (3) (114.4 g, 0.68 mol, yield 74%) was obtained.
Ethyl (4Z,6E)-octadienoate (3)
GC/MS (m/e); 168 (M$^+$, 55%), 123 (14), 94 (100), 81 (93), 79 (95), 67 (19), 55 (20), 41 (23)

(2) Reduction Step

[Chem. 54]

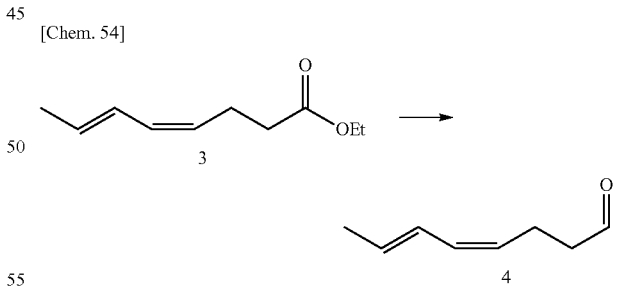

Ethyl (4Z,6E)-octadienoate (3) (26.9 g, 0.16 mol) and diethyl ether (250 ml) were added to a 500 ml capacity reaction vessel equipped with a dropping funnel and a stirrer, followed by cooling to −75° C. DIBAL (1.0 mol/l hexane solution, 195.8 ml, 0.192 mol) was put into the dropping funnel and added dropwise spending 3 hours so that the temperature did not rise. After completion of the dropwise addition, stirring was carried out for 30 minutes at the same temperature. 4 N hydrochloric acid aqueous solution (547 g) was cooled to 0° C., and the reaction liquid was added this to stop the reaction. The water layer was extracted with ether (50 ml), and then the organic layer was washed once with saturated brine. The organic layer was dried with magnesium sulfate, followed by concentrating to obtain (4Z,6E)-octadienal (4) (20.0 g, purity 96%).

(4Z,6E)-octadienal (4)

GC/MS (m/e); 124 (M+, 72%), 109 (8), 96 (65), 81 (71), 79 (83), 67 (100), 53 (55), 41 (62)

(3) Wittig Reaction Step

[Chem. 55]

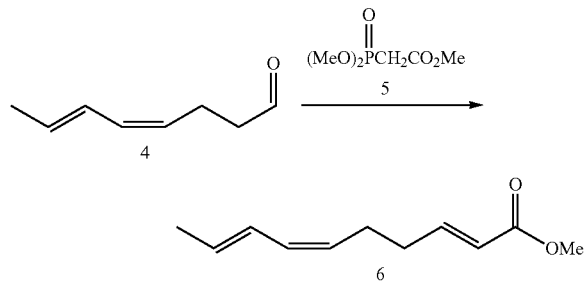

In a stream of nitrogen, sodium hydride (purity 55%, 7.37 g, 0.161 mol) and toluene (100 ml) were put into a 500 ml capacity flask equipped with a thermometer, a dropping funnel and a stirrer, followed by cooling to 0° C. The (4Z,6E)-octadienal (4) obtained in the above (20.0 g), trimethyl phosphonoacetate (30.8 g, 0.169 mol) and toluene (200 ml) were put into the dropping funnel and added dropwise spending 1.5 hours while keeping at 0° C. After completion of the dropwise addition, temperature was increased to room temperature (25° C.) and the stirring was further continued for 4 hours. After confirmation of the disappearance of aldehyde by a gas chromatography, 4 N hydrochloric acid aqueous solution (50 ml) was added thereto to carry out separation of liquid. The water layer was extracted twice with hexane (50 ml). The organic layers were combined, followed by washing twice with water (pH=5.5) and drying with magnesium sulfate. After filtration and concentration, distillation under a reduced pressure (75° C./0.5 ton) was carried out to obtain methyl (2E,6Z,8E)-decatrienoate (19.69 g, yield from the reduction reaction 68.3%).

Methyl (2E,6Z,8E)-decatrienoate

GC/MS (m/e); 180 (M+, 7%), 148 (7), 121 (6), 100 (24), 81 (100), 68 (8), 53 (23), 41 (22)

$^1$H-NMR (CDCl$_3$); δ 6.98 (dt, 1H, J=15.7, 6.6 Hz), 6.28 (m, 1H), 5.98 (dd, 1H, J=10.9 Hz), 5.91 (d, 1H, J=15.7 Hz), 5.70 (m, 1H), 5.25 (m, 1H), 3.73 (s, 3H), 2.2-2.4 (m, 4H), 1.78 (d, 3H, J=6.8 Hz)

$^{13}$C-NMR (CDCl$_3$); δ 167.01, 148.63, 130.09, 129.65, 127.22, 126.60, 121.30, 51.38, 32.27, 26.11, 18.27

(4) Amidation Step

[Chem. 56]

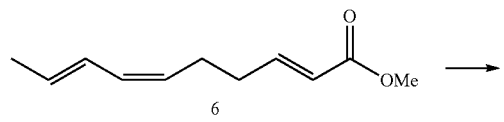

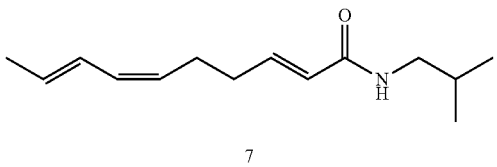

In an atmosphere of nitrogen, methyl 2,6,8-decatrienoate (6); 19.1 g {GC; 82.9%, pure amount; 15.9 g (0.0881 mol)} and 5 mol/l potassium hydroxide aqueous solution (60 ml, 0.30 mol) were added to a 200 ml capacity flask, followed by stirring at 70° C. for 2 hours. After completion of the reaction, the reaction was stopped with 5 mol/l hydrochloric acid (63 ml, 0.315 mol) and then extraction was carried out with toluene (32 ml) to obtain a 2,6,8-decatriene carboxylate/toluene solution.

In an atmosphere of nitrogen, the 2,6,8-decatrienic acid toluene solution obtained in the above and DMF (3.7 g, 0.05 mol) were added to a 100 ml capacity flask, followed by cooling to 5° C. Thionyl chloride (11.9 g, 0.10 mol) was added dropwise to this and stirring was carried out at 5° C. for 0.5 hour to obtain a toluene solution of 2,6,8-decatrienoic acid chloride.

In an atmosphere of nitrogen, isobutylamine (7.3 g, 0.10 mol), triethylamine (10.1 g, 0.10 mol) and toluene (32 ml) were added to a 200 ml capacity flask, followed by cooling to 5° C. Subsequently, the toluene solution of the 2,6,8-decatrienoic acid chloride (8) obtained in the above was added dropwise thereto, and stirring was carried out at 5° C. for 0.5 hour. After completion of the reaction, the reaction was stopped by adding water, and then the organic layer was separated and the organic layer was washed with 5% sodium carbonate aqueous solution, 0.1 mol/l sodium hydroxide aqueous solution and water in this order. The solvent was evaporated under a reduced pressure using an evaporator, and then the residue was purified by distillation under a reduced pressure (130 to 135° C./0.1 torr) to obtain spilanthol (7); 19.7 g {GC purity; 78.7%, pure amount; 15.5 g (0.0700 mol, yield 79%/(6))}.

2,6,8-Decatrienoic Acid

GC/MS (m/e); 166 (M+, 8%), 148 (2), 121 (2), 105 (2), 91 (4), 81 (100), 65 (5), 53 (18), 41 (16)

2,6,8-Decatrienoic Acid Chloride

GC/MS (m/e); 184 (M+, 6%), 149 (7), 121 (3), 105 (2), 93 (3), 81 (100), 68 (14), 53 (15), 41 (14)

Spilanthol (7)

GC/MS (m/e); 221 (M+, 10%), 206 (3), 192 (4), 178 (2), 167 (2), 141 (70), 126 (44), 98 (30), 81 (100), 69 (15), 53 (17), 41 (24)

$^1$H-NMR (CDCl$_3$); δ 6.82 (dt, 1H, J=15.3, 6.7 Hz), 6.28 (dd, 1H, J=10.7, 15.0 Hz), 5.97 (dd, 1H, J=10.7, 10.7 Hz), 5.87 (bs, 1H), 5.85 (d, 1H, J=15.3 Hz), 5.69 (dq, 1H, J=15.0, 6.7 Hz), 5.26 (dt, 1H, J=10.7, 6.8 Hz), 3.14 (dd, 2H, J=6.8, 6.8 Hz), 2.31 (dt, 2H, J=6.8, 6.8 Hz), 2.26 (dt, 2H, J=6.7, 6.8 Hz), 1.81 (dq, 1H, J=6.8, 6.8 Hz), 1.77 (d, 3H, J=6.7 Hz), 0.92 (d, 6H, J=6.7 Hz)

$^{13}$C-NMR (CDCl$_3$); δ 166.45, 143.74, 130.29, 129.83, 128.03, 127.09, 124.65, 47.26, 32.50, 28.97, 26.79, 20.53, 18.67

Example C2

Isobutyl Amidation by Enzyme

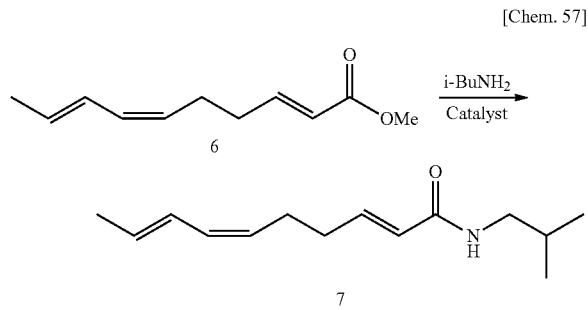

[Chem. 57]

The 2,6,8-decatrienoic acid methyl ester (6) prepared in Example C1; 10 g {GC purity; 96%, 2E,6Z,8E; 82.9%}, isobutylamine (4.0 g, 0.055 mol), Novozym 435 (5 g) and diisopropyl ether (10 ml) were added to a 50 ml capacity flask, and stirring was carried out at 35° C. for 4 days. After completion of the reaction and subsequent filtration of the enzyme, the solvent was evaporated under a reduced pressure using an evaporator, followed by distillation purification to obtain spilanthol (7); 11.1 g (2E,6Z,8E; 85.7%).

Example D1

(1) Wittig Reaction Step

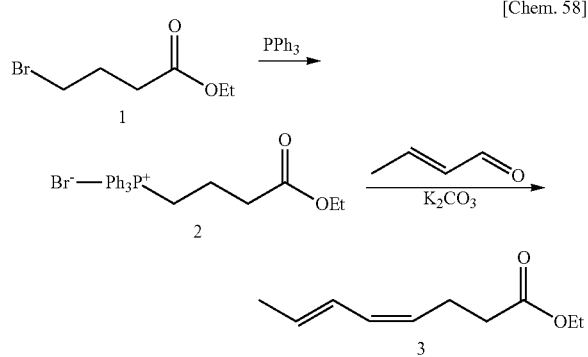

[Chem. 58]

In a stream of nitrogen, ethyl 4-bromobutanoate (1) (195 g, 1.0 mol), triphenylphosphine (288 g, 1.1 mol) and acetonitrile (195 ml) were put into a 1 liter capacity flask equipped with a reflux condenser, a stirrer and a thermometer, followed by heating to 90° C. and stirring for 40 hours. When the reaction solution was added dropwise to toluene (800 ml), followed by cooling to 20° C., a white solid was precipitated, and this solid was filtered and then drying under a reduced pressure (50° C./1 torr) was carried out to obtain a phosphonium salt (2) (420 g, 0.92 mol, yield 92%).

Ethyl 4-triphenylphosphoniumbutanoate Bromide (2)

$^1$H-NMR (CDCl$_3$): δ 1.23 (t, 31-1, J=7.2), 1.90-1.97 (m, 2H), 2.87 (t, 2H, J=6.3), 3.94-4.04 (m, 2H), 4.10 (q, 2H, J=7.2), 7.63-7.91 (m, 15H)

$^{31}$P-NMR (CDCl$_3$): δ 24.04

In a stream of nitrogen, the phosphonium salt (2) (420 g, 0.92 mol), toluene (1600 ml), potassium carbonate (506.2 g, 3.66 mol) and crotonaldehyde (256.7 g, 3.66 mol) were put into a 5 liter capacity flask equipped with a stirrer and a thermometer, followed by heating to 65° C. and stirring was continued for 7 hours. The reaction solution was cooled to room temperature, followed by mixing with water (840 g), stirring for 30 minutes and then subjecting to the separation of liquid. When the solvent of the organic layer was evaporated under a reduced pressure, a solid was precipitated, and the solid was removed by filtration. By distilling this solution under a reduced pressure (65 to 70° C./1.5 torr), ethyl (4Z, 6E)-octadienoate (3) (114.4 g, 0.68 mol, yield 74%) was obtained.

Ethyl (4Z,6E)-octadienoate (3)

GC/MS (m/e); 168 (M$^+$, 55%), 123 (14), 94 (100), 81 (93), 79 (95), 67 (19), 55 (20), 41 (23)

(2) Hydrolysis Step

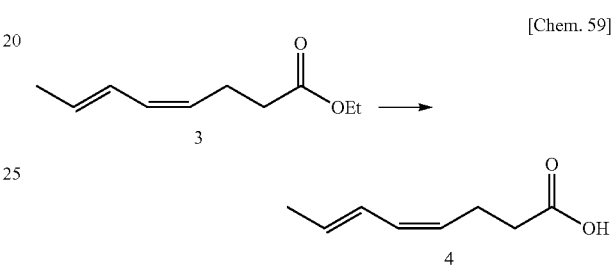

[Chem. 59]

20% Potassium hydroxide aqueous solution (477 g, 1.7 mol) and ethyl (4Z,6E)-octadienoate (3) (114.4 g, 0.68 mol) were put into a four neck distillation flask equipped with a thermometer and a stirrer, followed by heating to 45° C. and stirring was continued for 3 hour. By cooling the reaction solution to room temperature, heptane (230 ml) was added thereto, and 35% hydrochloric acid (177 g) was added dropwise thereto. After separation of liquid, washing with water was carried out once, and the solvent was evaporated under a reduced pressure to obtain (4Z,6E)-octadienoic acid (4) (90.6 g, 0.65 mol, yield 95%).

(4Z,6E)-Octadienoic Acid (4)

GC/MS (m/e); 140 (M$^+$, 68%), 122 (5), 95 (22), 81 (100), 79 (90), 67 (22), 53 (24), 41 (31)

(3) Mixed Anhydride Synthesis Step

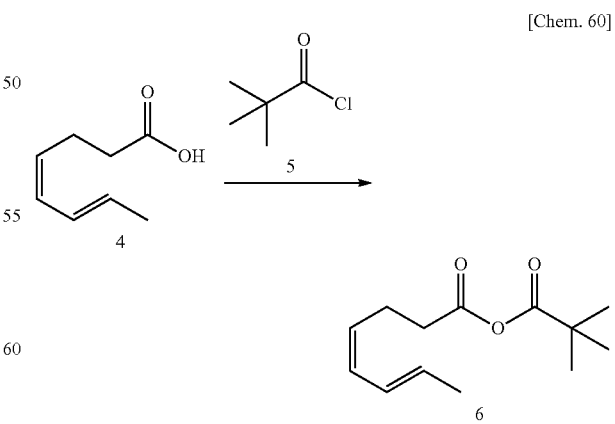

[Chem. 60]

In a stream of nitrogen, (4Z,6E)-octadienoic acid (4) (90.6 g, 0.65 mol), toluene (720 ml) and pivaloyl chloride (5) (85.7 g, 0.0.71 mol) were added to a 2 liter capacity reaction vessel equipped with a thermometer, a stirrer and a dropping funnel, followed by cooling to 5° C. Triethylamine (71.9 g, 0.71 mol) was added dropwise from the dropping funnel spending 1 hour, and then the temperature was gradually increased to room temperature, followed by stirring for 2 hours. After three times of washing with water and subsequent concentration, 139.8 g of crude pivaloyl (4Z,6E)-octadienoate acid anhydride (6) was obtained.

Pivaloyl (4Z,6E)-octadienoate acid anhydride (6)
GC/MS (m/e); 224 (M+, 3%), 196 (3), 140 (68), 123 (97), 94 (88), 81 (100), 57 (98), 51 (51)

(4) Carbon Increase Reaction Step

[Chem. 61]

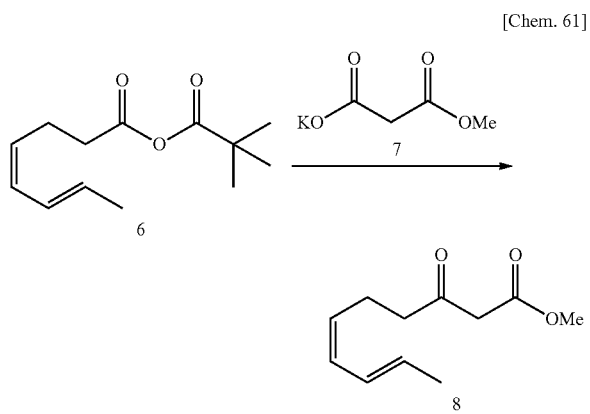

The crude pivaloyl (4Z,6E)-octadienoate acid anhydride (6) obtained in the above (139.8 g), THF (140 ml) and triethylamine (69.3 g, 0.685 mol) were put into a 500 ml capacity flask equipped with a stirrer and a thermometer, followed by cooling to 5° C., and imidazole (45.2 g, 0.72 mol) was added thereto, followed by stirring for 1 hour.

In a stream of nitrogen, magnesium chloride (75.3 g, 0.79 mol), THF (560 ml) and methyl malonate mono-potassium salt (7) (155 g, 0.996 mol) were put into a 2 liter capacity flask equipped with a dropping funnel, a stirrer and a thermometer, and the reaction solution described in the above was added dropwise thereto from the dropping funnel, spending 1 hour, followed by further stirring for 5 hours. 35% Hydrochloric acid aqueous solution (265 g, 2.55 mol) was added dropwise thereto, followed by separation of liquid and subsequent washing twice with 10% sodium carbonate aqueous solution. The solvent was evaporated under a reduced pressure, and distillation under a reduced pressure (90° C./0.5 torr) was carried out to obtain methyl 3-oxo-6,8-decadienoate (8) (88.8 g, yield 70%).

Methyl 3-oxo-6,8-decadienoate (8)
GC/MS (m/e); 196 (M+, 15%), 178 (8), 164 (12), 146 (18), 135 (8), 122 (88), 101 (20), 94 (78), 81 (56), 79 (100), 55 (20), 41 (22)

(5) Reduction Step

[Chem. 62]

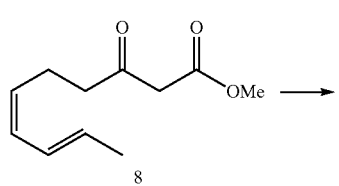

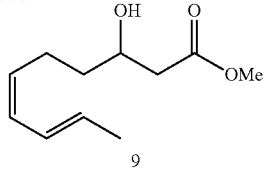

In a stream of nitrogen, sodium borohydride (5.1 g, 0.14 mol) and THF (360 ml) were put into a 1 liter capacity flask equipped with a stirrer, a dropping funnel and a thermometer, followed by cooling to 0° C., and methyl 3-oxo-6,8-decadienoate (8) (88.8 g, 0.45 mol) was added dropwise thereto from the dropping funnel, spending 1 hour. After completion of the dropwise addition, 35% hydrochloric acid aqueous solution (47 g) was added dropwise thereto, followed by extraction twice with ethyl acetate (180 ml). The organic layer was washed with water and then the solvent was evaporated under a reduced pressure to obtain methyl 3-hydroxy-6,8-decadienoate (9) (86.1 g, 0.43 mol, yield 96%).

Methyl 3-hydroxy-6,8-decadienoate (9)
GC/MS (m/e); 198 (M+, 6%), 180 (45), 165 (3), 149 (12), 129 (13), 120 (40), 106 (100), 91 (72), 79 (95), 67 (33), 55 (39), 41 (40)

(6) Amidation Step

[Chem. 63]

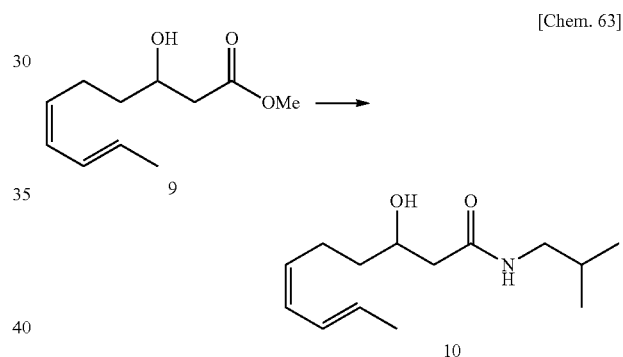

Methyl 3-hydroxy-6,8-decadienoate (9) (86.1 g, 0.43 mol) and isobutylamine (95.3 g, 1.3 mol) were put into a 500 ml capacity flask equipped with a stirrer, a thermometer and a reflux condenser, followed by heating to 90° C. and stirring for 24 hours. After recovering isobutylamine under a reduced pressure, and when heptane (700 ml) was added, followed by cooling to 0° C., a white solid was precipitated. This solid was filtered and dried under a reduced pressure to obtain N-isobutyl-3-hydroxy-6,8-decadienamide (10) (85.2 g, 0.35 mol, yield 82%).

GC/MS (m/e); 239 (M+, 45%), 221 (40), 206 (12), 192 (7), 170 (5), 157 (8), 144 (12), 128 (7), 115 (62), 107 (43), 81 (52), 79 (85), 57 (100), 55 (30), 41 (53), 30 (54)

(7) Sulfonic Acid Esterification Step

[Chem. 64]

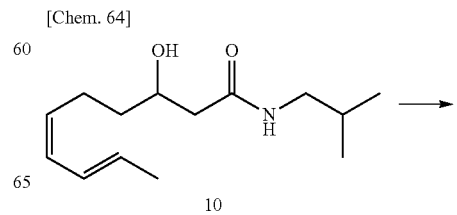

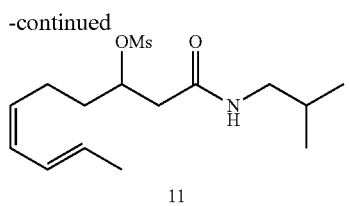

In a stream of nitrogen, N-isobutyl-3-hydroxy-6,8-decadienamide (10) (85.2 g, 0.35 mol), ethyl acetate (680 ml) and triethylamine (72.1 g, 0.70 mol) were put into a 1 liter capacity flask equipped with a stirrer, a thermometer and a dropping funnel, followed by cooling to 5° C., and then methanesulfonyl chloride (44.7 g, 0.392 mol) was added dropwise thereto spending 1 hour. After completion of the dropwise addition, water (170 ml) was added thereto to carry out separation of liquid. By further washing three times with water and evaporating the solvent under a reduced pressure, N-isobutyl-3-sulfonyloxy-6,8-decadienamide (11) was obtained (108.9 g, yield 98%).

N-Isobutyl-3-sulfonyloxy-6,8-decadienamide (11)

GC/MS (m/e); 317 (M$^+$, 3%), 301 (18), 288 (2), 260 (3), 243 (1), 222 (48), 206 (12), 192 (7), 178 (5), 155 (4), 141 (18), 128 (40), 115 (50), 107 (53), 93 (63), 79 (80), 57 (100), 41 (68)

(8) Elimination Step

[Chem. 65]

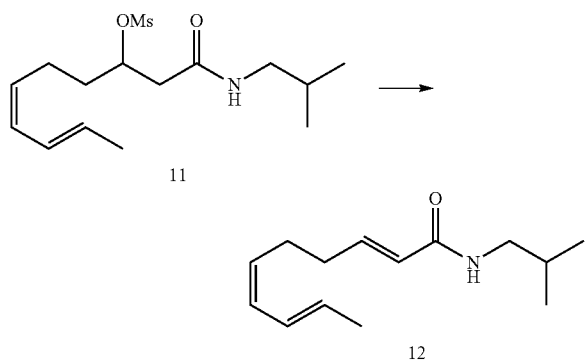

By spending 1 hour, a 28% sodium methoxide-methanol solution (75.5 g, 0.39 mol) was added dropwise to a solution prepared by dissolving N-isobutyl-3-sulfonyloxy-6,8-decadienamide (11) (108.9 g) in THF (425 ml) and cooling to 0° C., and further stirring was carried out for 2 hours after completion of the dropwise addition. After separation of liquid by adding water (170 g), washing with water was carried out twice and the solvent was evaporated under a reduced pressure to obtain a crude product. By distilling this crude product under a reduced pressure (140° C./0.3 ton), N-isobutyl-2,6,8-decatrienamide (12) was obtained (58.8 g, 0.27 mol, purity 98.9%).

N-isobutyl-2,6,8-decatrienamide (12)

GC/MS (m/e); 221 (M$^+$, 10%), 206 (3), 192 (4), 178 (2), 167 (2), 141 (70), 126 (44), 98 (30), 81 (100), 69 (15), 53 (17), 41 (24)

$^1$H-NMR (CDCl$_3$); δ 6.82 (dt, 1H, J=15.3, 6.7 Hz), 6.28 (dd, 1H, J=10.7, 15.0 Hz), 5.97 (dd, 1H, J=10.7, 10.7 Hz), 5.87 (bs, 1H), 5.85 (d, 1H, J=15.3 Hz), 5.69 (dq, 1H, J=15.0, 6.7 Hz), 5.26 (dt, 1H, J=10.7, 6.8 Hz), 3.14 (dd, 2H, J=6.8, 6.8 Hz), 2.31 (dt, 2H, J=6.8, 6.8 Hz), 2.26 (dt, 2H, J=6.7, 6.8 Hz), 1.81 (dq, 1H, J=6.8, 6.8 Hz), 1.77 (d, 3H, J=6.7 Hz), 0.92 (d, 6H, J=6.7 Hz)

While the invention has been described in detail and with reference to specific embodiments thereof, it will be apparent to one skilled in the art that various changes and modifications can be made therein without departing from the spirit and scope of the invention.

This application is based on a Japanese patent application filed on Jan. 18, 2008 (Japanese Patent Application No. 2008-009295), a Japanese patent application filed on Jan. 18, 2008 (Japanese Patent Application No. 2008-009832), a Japanese patent application filed on Jan. 18, 2008 (Japanese Patent Application No. 2008-009821) and a Japanese patent application filed on Jan. 18, 2008 (Japanese Patent Application No. 2008-009851), the entire contents thereof being thereby incorporated by reference.

INDUSTRIAL APPLICABILITY

By the invention, it becomes possible to industrially carry out production of spilanthol without using expensive reagents and without mediating purification steps such as column chromatography. The spilanthol obtained in the invention is useful as a flavor or fragrance component.

The invention claimed is:

1. A production method of N-isobutyl-2,6,8-decatrienamide, wherein a column chromatography purification step is not required in all processes.

2. The production method according to claim 1, wherein all processes are carried out at a reaction temperature of −20° C. or more.

3. The production method according to claim 1, wherein a chemical purity of the N-isobutyl-2,6,8-decatrienamide is 80% or more, and a content of a 2E,6Z,8E-isomer of the N-isobutyl-2,6,8-decatrienamide is 65% or more.

4. The production method of N-isobutyl-2,6,8-decatrienamide according to claim 3, which comprises:

(AI) preparing a β-hydroxycarboxylic acid ester represented by the formula (A2) by reducing a β-keto ester represented by the formula (A1) (reduction step),

[Chem. 1]

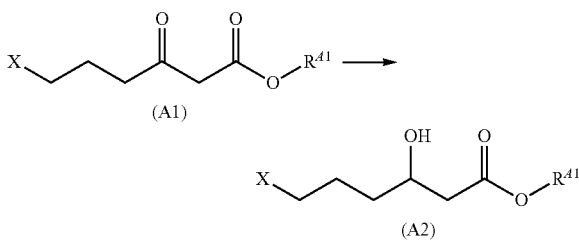

(in the formula (A1) and formula (A2), X represents a chlorine atom or a bromine atom and R$^{41}$ represents an alkyl group having from 1 to 4 carbon atoms);

(AII) preparing a β-sulfonyloxycarboxylic acid ester represented by the formula (A3) by sulfonic acid esterification of the β-hydroxycarboxylic acid ester represented by the formula (A2) (sulfonic acid esterification step),

[Chem. 2]

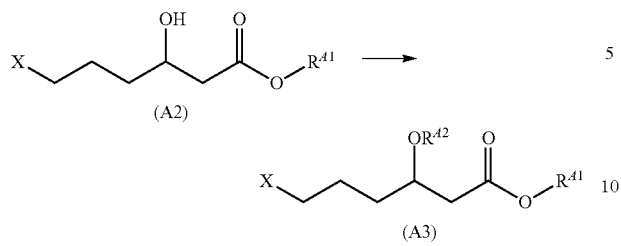

(in the formula (A2), X and $R^{A1}$ are as defined in the foregoing, and in the formula (A3), X represents a chlorine atom or a bromine atom, $R^{A1}$ represents an alkyl group having from 1 to 4 carbon atoms and $R^{A2}$ represents an alkanesulfonyl group, a benzenesulfonyl group or a toluenesulfonyl group);

(AIII) preparing an α,β-unsaturated carboxylic acid ester represented by the formula (A4) from the β-sulfonyloxycarboxylic acid ester represented by the formula (A3) under a basic condition (elimination step),

[Chem. 3]

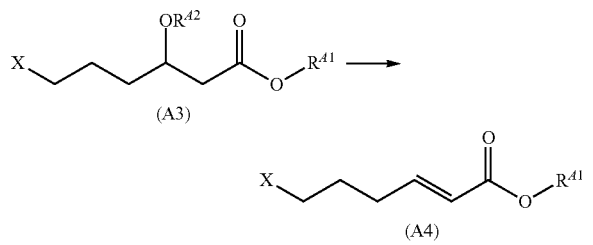

(in the formula (A3), X, $R^{A1}$ and $R^{A2}$ are as defined in the foregoing, and in the formula (A4), X represents a chlorine atom or a bromine atom and $R^{A1}$ represents an alkyl group having from 1 to 4 carbon atoms);

(AIV) preparing a (2E,6Z,8E)-decatrienoic acid ester represented by the formula (A6) by allowing a phosphonium salt represented by the formula (A5), which is derived from the α,β-unsaturated carboxylic acid ester represented by the formula (A4), to react with crotonaldehyde under a basic condition (Wittig reaction step),

[Chem. 4]

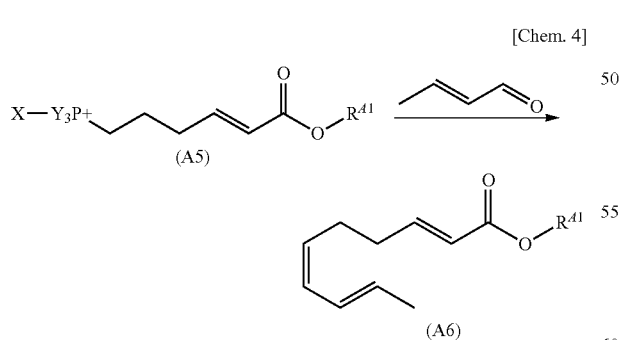

(in the formula (A5), X represents a chlorine atom or a bromine atom, Y represents an alkyl group or an aryl group which may have a substituent group, and $R^{A1}$ represents an alkyl group having from 1 to 4 carbon atoms, and in the formula (A6), $R^{A1}$ represents an alkyl group having from 1 to 4 carbon atoms); and (AV) obtaining (2E,6Z,8E)-N-isobutyl-2,6,8-decatrienamide by allowing the decatrienoic acid ester represented by the formula (A6) to react with isobutylamine in the presence of a catalyst, or by hydrolyzing the decatrienoic acid ester represented by the formula (A6), converting said acid thereafter into an acid halide, and allowing this acid halide to react with isobutylamine (amidation step).

5. The production method according to claim 4, wherein the base which is used in the Wittig reaction step of (AIV) is potassium carbonate.

6. The production method of N-isobutyl-2,6,8-decatrienamide production method according to claim 3, which comprises:

(BI) preparing a hydroxyacetal represented by the formula (B2) by acetalization reaction and hydrolysis of an acyloxybutanal represented by the formula (B1) (acetalization step),

[Chem. 5]

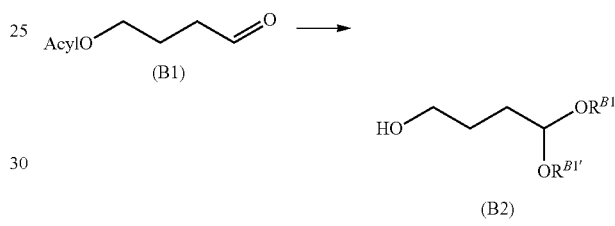

(in the formula (B1), Acyl represents an acyl group having from 2 to 5 carbon atoms, and in the formula (B2), $R^{B1}$ and $R^{B1'}$ each independently represents an alkyl group having from 1 to 4 carbon atoms, or $R^{B1}$ and $R^{B1'}$ may form a divalent carbon chain which may have a substituent group);

(BII) preparing a sulfonic acid ester represented by the formula (B3) (sulfonic acid esterification step),

[Chem. 6]

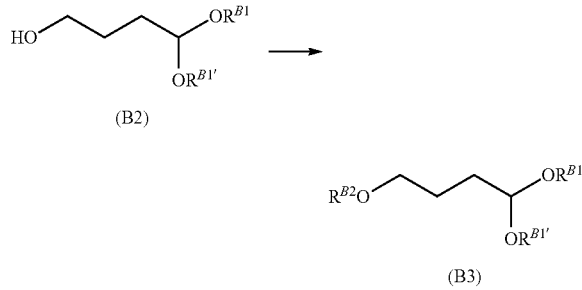

(in the formula (B2), $R^{B1}$ and $R^{B1'}$ are as defined in the foregoing, and in the formula (B3), $R^{B1}$ and $R^{B1'}$ each independently represents an alkyl group having from 1 to 4 carbon atoms, or $R^{B1}$ and $R^{B1'}$ may form a divalent carbon chain which may have a substituent group, and $R^{B2}$ represents an alkanesulfonyl group, a benzenesulfonyl group or a toluenesulfonyl group);

(BIII) preparing a halide represented by the formula (B4) (halogenation step),

[Chem. 7]

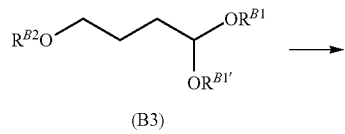

(B3)

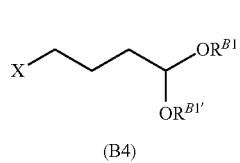

(B4)

(in the formula (B3), $R^{B1}$, $R^{B1'}$ and $R^{B2}$ are as defined in the foregoing, and in the formula (B4), $R^{B1}$ and $R^{B1'}$ each independently represents an alkyl group having from 1 to 4 carbon atoms, or $R^{B1}$ and $R^{B1'}$ may form a divalent carbon chain which may have a substituent group, and X represents a halogen atom);

(BIV) preparing an acetal of a (4Z,6E)-octadienal represented by the formula (B6) by allowing a phosphonium salt (formula (B5)) which is derived from the formula (B4) to react with crotonaldehyde under a basic condition (Wittig reaction step),

[Chem. 8]

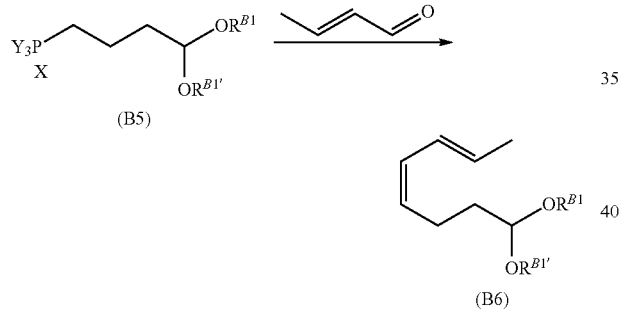

(in the formula (B5), $R^{B1}$, $R^{B1'}$ and X are as defined in the foregoing and Y represents an alkyl group or an aryl group which may have a substituent group, and in the formula (B6), $R^{B1}$ and $R^{B1'}$ each independently represents an alkyl group having from 1 to 4 carbon atoms, or $R^{B1}$ and $R^{B1'}$ may form a divalent carbon chain which may have a substituent group);

(BV) preparing a (4Z,6E)-octadienal represented by the formula (B7) by deprotecting the octadiene acetal represented by the formula (6) in the presence of an acid catalysis (deprotection step),

[Chem. 9]

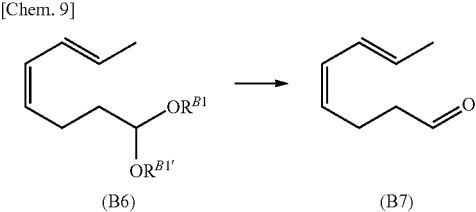

(in the formula (B6), $R^{B1}$ and $R^{B1'}$ are as defined in the foregoing);

(BVI) preparing a mixture of N-isobutyl-2,6,8-decatrienamide and N-isobutyl-3,6,8-decatrienamide represented by the formula (B8), by allowing a (4Z,6E)-octadienal represented by the formula (B7) and malonic acids to undergo condensation under a basic condition,

[Chem. 10]

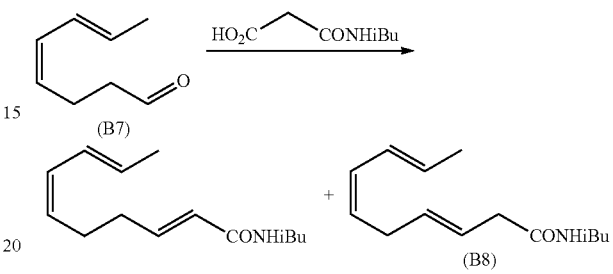

wherein monoisobutyl malonate amide is allowed to undergo the reaction as the malonic acids, (Knoevenagel step 1); and (BVII) isomerizing the N-isobutyl-3,6,8-decatrienamide represented by the formula (B8),

[Chem. 11]

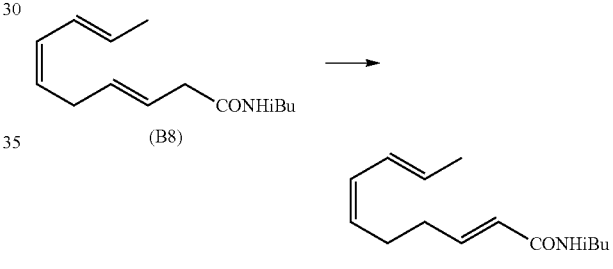

in the mixture of a positional isomer of N-isobutyldecatrienamide obtained in the aforementioned step (VI), into N-isobutyl-2,6,8-decatrienamide (spilanthol) under a basic condition (isomerization step).

7. The production method according to claim 6, the method comprising:

preparing a decatrienoic acid ester or decatrienoic acid represented by the formula (B9) by allowing malonic acid or a malonic acid monoester as the malonic acids in the step (BVI) described in claim 6 under a basic condition (Knoevenagel step 2),

[Chem. 12]

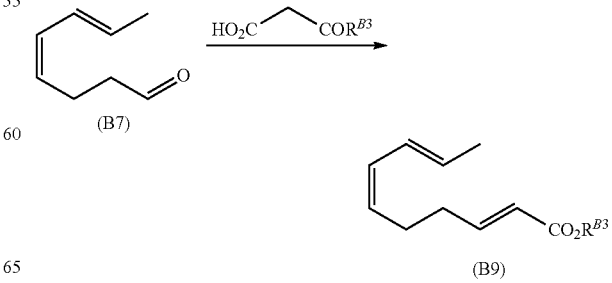

(in the formula (B9), $R^{B3}$ represents a hydrogen atom or an alkyl group having from 1 to 4 carbon atoms); and obtaining (2E,6Z,8E)-N-isobutyl-2,6,8-decatrienamide by allowing the decatrienoic acid ester represented by the formula (B9) to react with isobutylamine in the presence of a catalyst, or by hydrolyzing the decatrienoic acid and decatrienoic acid ester represented by the formula (B9), converting the thus obtained decatrienoic acid into an acid halide and then allowing isobutylamine to act thereon (amidation step).

8. The production method according to claim 6, wherein the base which is used in the Wittig reaction step of the aforementioned step (BIV) is potassium carbonate.

9. The production method of N-isobutyl-2,6,8-decatrienamide according to claim 3, which comprises:

(DI) preparing a (4Z,6E)-octadienoic acid ester represented by the general formula (D3) by allowing a phosphonium salt represented by the general formula (D2), which is derived from a 4-halobutanoic acid ester represented by the general formula (D1), to react with crotonaldehyde under a basic condition (Wittig reaction step),

[Chem. 17]

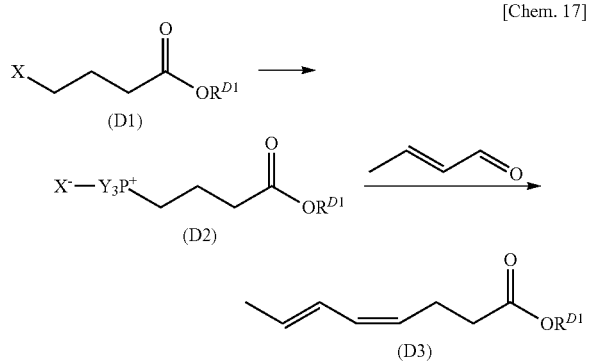

(in the formulae, $R^{D1}$ is an alkyl group having from 1 to 4 carbon atoms; X is a chlorine atom or a bromine atom; and Y is an alkyl group or an aryl group which may have a substituent group);

(DII) preparing (4Z,6E)-octadienoic acid represented by the formula (D4) by hydrolyzing the (4Z,6E)-octadienoic acid ester represented by the general formula (D3) (hydrolysis step),

[Chem. 18]

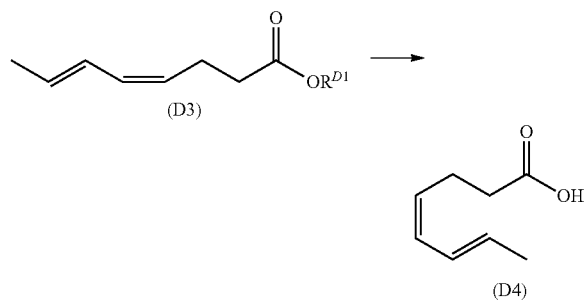

(in the formula, $R^{D1}$ is as defined in the foregoing);

(DIII) preparing a mixed anhydride represented by the general formula (D6) by allowing the 4,6-octadienoic acid represented by the formula (D4) to react with an acid halide represented by the general formula (D5) under a basic condition (mixed anhydride synthesis step),

[Chem. 19]

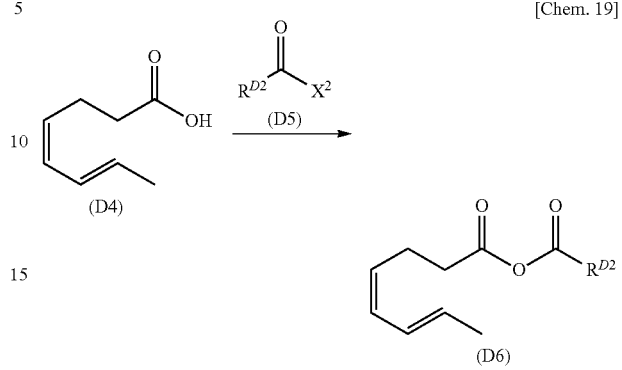

(in the formulae, $R^{D2}$ is an alkyl group having from 1 to 4 carbon atoms; and $X^2$ is a chlorine atom or a bromine atom);

(DIV) preparing a 3-oxo-6,8-decadienoic acid ester represented by the general formula (D8) by allowing the mixed anhydride represented by the general formula (D6) to react with a salt of a malonic acid monoester represented by the general formula (D7) (carbon increase step),

[Chem. 20]

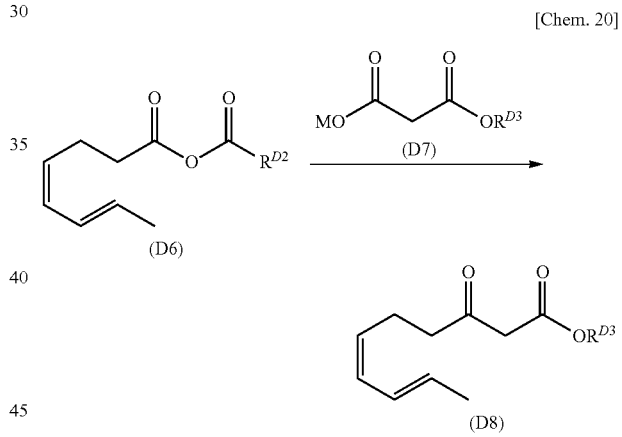

(in the formulae, $R^{D2}$ is as defined in the foregoing; $R^{D3}$ is an alkyl group having from 1 to 4 carbon atoms; and M is sodium or potassium);

(DV) preparing a 3-hydroxy-6,8-decadienoic acid ester represented by the general formula (D9) by reducing a ketone moiety of the 3-oxo-6,8-decadienoic acid ester represented by the general formula (D8) (reduction step),

[Chem. 21]

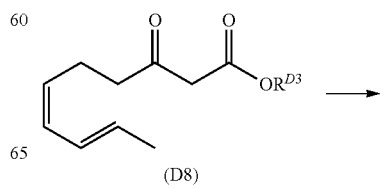

-continued

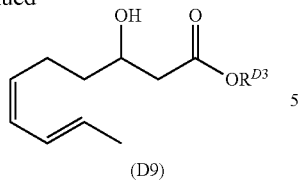

(D9)

(in the formulae, $R^{D3}$ is as defined in the foregoing);

(DVI) preparing an N-isobutyl-3-hydroxy-6,8-decadienamide represented by the formula (D10) by allowing the 3-hydroxy-6,8-decadienoic acid ester represented by the general formula (D9) to react with isobutylamine (amidation step),

[Chem. 22]

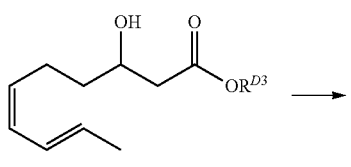
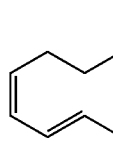

(D9)

(D10)

(in the formulae, $R^{D3}$ is as defined in the foregoing);

(DVII) preparing an N-isobutyl-3-sulfonyloxy-6,8-decadienamide represented by the general formula (D11) by subjecting the N-isobutyl-3-hydroxy-6,8-decadienamide represented by the formula (D10) to sulfonic acid esterification (sulfonic acid esterification step),

[Chem. 23]

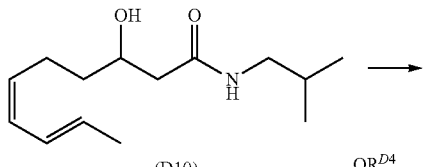
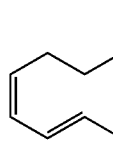

(D10)

(D11)

(in the formulae, $R^{D4}$ is an alkanesulfonyl group, a benzenesulfonyl group or a toluenesulfonyl group); and (DVIII) obtaining (2E,6Z,8E)-N-isobutyl-2,6,8-decatrienamide represented by the formula (D12) by treating the N-isobutyl-3-sulfonyloxy-6,8-decadienamide represented by the general formula (D11) with a base under a basic condition (elimination step),

[Chem. 24]

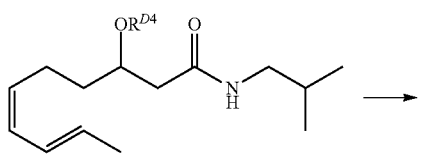

(D11)

-continued

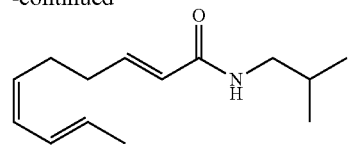

(D12)

(in the formulae, $R^{D4}$ is as defined in the foregoing).

10. The production method according to claim 9, wherein the base which is used in the Wittig reaction step of (DI) is potassium carbonate.

11. A flavor or fragrance composition, food or drink, fragrance or cosmetic, or pharmaceutical, which comprises the N-isobutyl-2,6,8-decatrienamide which is produced by the method according to any one of claims 3, 4, 5, 6, 7, 8, 9 or 10.

12. A β-sulfonyloxycarboxylic acid ester represented by the formula (A3):

[Chem. 25]

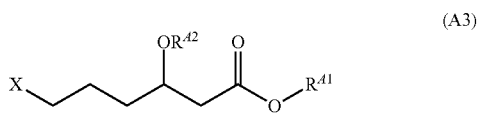

(A3)

(in the formula (A3), X represents a chlorine atom or a bromine atom, $R^{A1}$ represents an alkyl group having from 1 to 4 carbon atoms, and $R^{A2}$ represents an alkanesulfonyl group, a benzenesulfonyl group or a toluenesulfonyl group).

13. A decatrienoic acid halide represented by the formula (A8):

[Chem. 26]

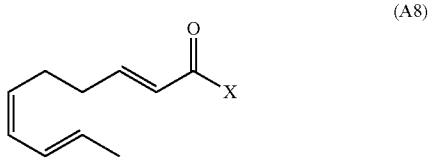

(A8)

(in the formula (A8), X represents a chlorine atom or a bromine atom).

14. An acetal of octadienal represented by the formula (B6):

[Chem. 28]

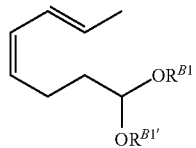

(B6)

(in the formula, $R^{B1}$ and $R^{B1'}$ each independently represent an alkyl group having from 1 to 4 carbon atoms, or $R^{B1}$ and $R^{B1'}$ may form a divalent carbon chain which may have a substituent group).

15. An N-isobutyl-3-hydroxy-6,8-decadienamide represented by the formula (D10):
[Chem. 29]
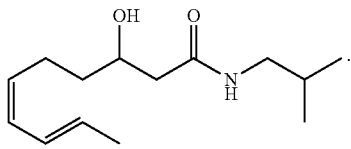
(D10)
16. An N-isobutyl-3-sulfonyloxy-6,8-decadienamide represented by the formula (D11):
[Chem. 30]
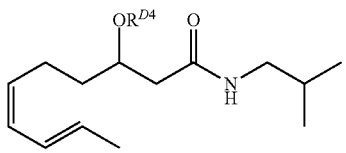
(D11)
(in the formula, $R^{D4}$ is an alkanesulfonyl group, a benzenesulfonyl group or a toluenesulfonyl group).
* * * * *